(12) United States Patent
Boschelli et al.

(10) Patent No.: US 7,479,561 B2
(45) Date of Patent: Jan. 20, 2009

(54) 4-(2,4-DICHLORO-5-METHOXYPHENYL) AMINO-6-METHOXY-7-{[5-SUBSTITUTED-AMINO)METHYL]-3-FURYL}-3-QUINOLINECARBONITRILES AS KINASE INHIBITORS

(75) Inventors: Diane Harris Boschelli, New City, NY (US); Jay Thomas Afragola, Spring Valley, NY (US); Asaf Alimardanov, Nanuet, NY (US); Biqi Wu, Nanuet, NY (US)

(73) Assignee: Wyeth, Madison, NJ (US)

( * ) Notice: Subject to any disclaimer, the term of this patent is extended or adjusted under 35 U.S.C. 154(b) by 624 days.

(21) Appl. No.: 11/201,705

(22) Filed: Aug. 11, 2005

(65) Prior Publication Data

US 2006/0035930 A1     Feb. 16, 2006

Related U.S. Application Data

(60) Provisional application No. 60/601,825, filed on Aug. 16, 2004.

(51) Int. Cl.
*C07D 215/38*     (2006.01)
(52) U.S. Cl. ..................... 546/159; 546/160
(58) Field of Classification Search ............... 546/159, 546/160; 514/312, 313
See application file for complete search history.

(56) References Cited

U.S. PATENT DOCUMENTS

| | | |
|---|---|---|
| 6,521,618 B2 | 2/2003 | Boschelli et al. |
| 2002/0026052 A1 | 2/2002 | Boschelli et al. |

FOREIGN PATENT DOCUMENTS

| | | | |
|---|---|---|---|
| WO | 01/72711 | * | 10/2001 |
| WO | WO 2005/019201 A2 | | 3/2005 |

OTHER PUBLICATIONS

Boschelli, D. H., et al.; Bioorganic & Medicinal Chemistry Letters 12:2011-2014 (2002).
Chiarello, J.; et al.; Tetrahedron 44(1):41-48 (1988).
Golas, J. M.; et al.; Cancer Research 63:375-381 (2003).

* cited by examiner

*Primary Examiner*—D. Margaret Seaman
(74) *Attorney, Agent, or Firm*—David Rubin

(57) ABSTRACT

This invention relates to compounds having the structure of Formula I

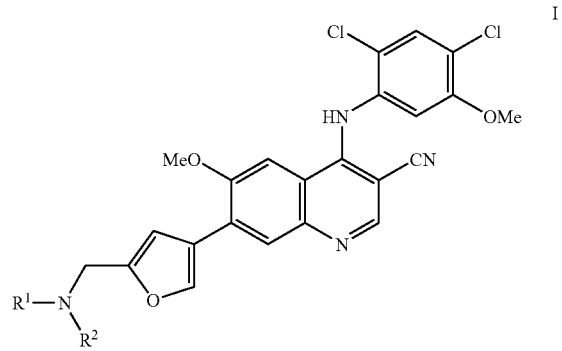

wherein $R^1$, $R^2$, $R^3$, and $R^4$ are described herein.

40 Claims, No Drawings

4-(2,4-DICHLORO-5-METHOXYPHENYL) AMINO-6-METHOXY-7-{[5-SUBSTITUTED-AMINO)METHYL]-3-FURYL}-3-QUINOLINECARBONITRILES AS KINASE INHIBITORS

This application claims priority from provisional application Ser. No. 60/601,825, filed Aug. 16, 2004, the entire disclosure of which is hereby incorporated by reference.

BACKGROUND OF THE INVENTION

This invention relates to compounds that inhibit the activity of protein kinases. Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration. Specific protein kinases have been implicated in diverse conditions including cancer [Blume-Jensen, P., Nature, 411, 355 (2001)) Traxler, P. M., Exp. Opin. Ther. Patents, 8, 1599 (1998); Bridges, A. J., Emerging Drugs, 3, 279 (1998)]; restenosis [Mattsson, E., Trends Cardiovascular Medicine 5, 200 (1995)]; atherosclerosis [Raines, E. W., Bioessays, 18, 271 (1996)]; angiogenesis [Shawver, L. K., Drug Discovery Today, 2, 50 (1997); Folkman, J., Nature Medicine, 1, 27 (1995)] stroke [Paul, R., Nature Medicine 7, 222 (2001)]; and osteoporosis [Boyce, J. Clin. Invest., 90, 1622 (1992)].

Tyrosine kinases (TK) are a class of protein kinases. The major family of cytoplasmic protein TKs is the Src family which consists of at least eight members (Src, Fyn, Lyn, Yes, Lck, Fgr, Hck and Blk) that participate in a variety of signaling pathways [Schwartzberg, P. L., Oncogene, 17, 1463 (1998)]. The prototypical member of this tyrosine kinase family is Src, which is involved in proliferation and migration responses in many cell types [Sawyer, T., Expert Opin. Investig. Drugs, 10, 1327 (2001)]. Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley, C. A., Cell Growth Differentiation, 8, 269 (1997)], suggesting that Src inhibitors could slow tumor growth. In addition to its role in cell proliferation, Src also acts in stress response pathways, including the hypoxia response. Nude mice studies with colon tumor cells expressing antisense Src message have reduced vascularization [Ellis, L. M., J. Biol. Chem., 273, 1052 (1998)], which suggests that Src inhibitors could be anti-angiogenic as well as anti-proliferative.

Src disrupts E-cadherin associated cell-cell interactions [E. Avezienyte, Nature Cell Bio., 4, 632 (2002)]. A low molecular weight Src inhibitor prevents this disruption thereby reducing cancer cell metastasis [Nam, J. S., Clinical Cancer Res., 8, 2340 (2002)].

Src inhibitors may prevent the secondary injury that results from a VEGF-mediated increase in vascular permeability such as that seen following stroke [Eliceiri, B. P., Mol. Cell., 4, 915 (1999); Paul, R., Nat. Med. 7, 222 (2001)].

Src also plays a role in osteoporosis. Mice genetically engineered to be deficient in Src production were found to exhibit osteopetrosis, the failure to resorb bone [Soriano, P., Cell, 64, 693 (1991); Boyce, B. F., J. Clin., Invest., 90, 1622 (1992)]. This defect was characterized by a lack of osteoclast activity. Since osteoclasts normally express high levels of Src, inhibition of Src kinase activity may be useful in the treatment of osteoporosis [Missbach, M., Bone, 24, 437 (1999)].

Inhibitors of the NMDA (N-methyl-D-asparte) receptor could provide treatment of chronic neuropathic pain [Urban, L. Drug Dev. Res., 54, 159 (2002)]. The activity of NMDA receptors is regulated by Src family kinases (SFKs) (Yu, X. M., Proc. Nat. Acad. Sci., U.S.A., 96, 7697 (1999) and a low molecular weight SFK inhibitor, PP2, decreases phosphorylation of the NMDA receptor NR2 subunit [Guo, W. J. Neuro., 22(14), 6208 (2002)]. SFK inhibitors therefore have potential in the treatment of neuropathic pain.

Tyrosine kinases (TKs) are divided into two classes: the non-transmembrane TKs and transmembrane growth factor receptor TKs (RTKs) [Blume-Jensen, P., Nature, 411, 355 (2001)]. Growth factors, such as epidermal growth factor (EGF), bind to the extracellular domain of their partner RTK on the cell surface which activates the RTK, initiating a signal transduction cascade that controls a wide variety of cellular responses including proliferation and migration. The overexpression of EGF and also of members of the epidermal growth factor receptor (EGFr) family, which includes EGF-r, erbB-2, erbB-3 and erbB-4, is implicated in the development and progression of cancer [Rusch, V., Cytokine Growth Factor Rev., 7, 133 (1996), Davies, D. E., Biochem. Pharmacol., 51, 1101 (1996) and Modjtahedi, E., Int. J. Oncol., 4, 277 (1994)]. Specifically, over expression of the receptor kinase product of the erbB-2 oncogene has been associated with human breast and ovarian cancers [Slamon, D. J., Science, 244, 707 (1989) and Slamon, D. J., Science, 235, 177 (1987)]. Upregulation of EGFr kinase activity has been associated with epidermoid tumors [Reiss, M., Cancer Res., 51, 6254 (1991)]; breast tumors [Macias, A., Anticancer Res., 7, 459 (1987)]; and tumors involving other major organs [Gullick, W. J., Brit. Med. Bull., 47, 87 (1991)].

It is also known that deregulation of EGF receptors is a factor in the growth of epithelial cysts in the disease described as polycystic kidney disease [Du, J., Amer. J. Physiol., 269 (2 Pt 1), 487 (1995); Nauta, J., Pediatric Res., 37(6), 755 (1995); Gattone, V. H., Developmental Biology, 169(2), 504 (1995); Wilson, P. D., Eur. J. Cell Biol., 61(1), 131, (1993)]. The compounds of this invention, which inhibit the catalytic function of the EGF receptors, are consequently useful for the treatment of this disease.

In addition to EGFr, there are several other RTKs including FGFr, the receptor for fibroblast growth factor (FGF); flk-1, also known as KDR, and flt-1, the receptors for vascular endothelial growth factor (VEGF); and PDGFr, the receptor for platelet derived growth factor (PDGF). The formation of new blood vessels, a process known as angiogenesis, is essential for tumor growth. Two natural angiogenesis inhibitors, angiostatin and endostatin, dramatically inhibited the growth of a variety of solid tumors. [O'Reilly, M. S., Cell, 79, 315 (1994); O'Reilly, M. S., Nature Medicine, 2, 689 (1996); O'Reilly, M. S., Cell, 88, 277 (1997)]. Since FGF and VEGF are known to stimulate angiogenesis, inhibition of the kinase activity of their receptors should block the angiogenic effects of these growth factors. In addition, the receptor tyrosine kinases tie-1 and tie-2 also play a key role in angiogenesis [Sato, T. N., Nature, 376, 70 (1995)]. Compounds of the invention that inhibit the kinase activity of FGFr, flk-1, flt-1, tie-1 or tie-2 may inhibit tumor growth by their effect on angiogenesis.

PDGF is a potent growth factor and chemoattractant for smooth muscle cells (SMCs). The renarrowing of coronary arteries following angioplasty is due in part to the enhanced proliferation of SMCs in response to increased levels of PDGF. Therefore, compounds that inhibit the kinase activity of PDGFr may be useful in the treatment of restenosis. In addition, since PDGF and PDGFr are overexpressed in several types of human gliomas, small molecules capable of suppressing PDGFr activity, have potential utility as anticancer therapeutics [Nister, M., *J. Biol. Chem.* 266, 16755 (1991); Strawn, L. M., *J. Biol. Chem.* 269, 21215 (1994)].

Other RTKs that could potentially be inhibited by compounds of this invention include colony stimulating factor receptor, the nerve growth factor receptors (trka, trkB and trkC), the insulin receptor, the insulin-like growth factor receptor, the hepatocyte growth factor receptor and the erythropoietin-producing hepatic cell receptor (EPH).

In addition to the RTKs there is another family of TKs termed the cytoplasmic protein or non-receptor TKs. The cytoplasmic protein TKs have intrinsic kinase activity, are present in the cytoplasm and nucleus, and participate in diverse signaling pathways. There are a large number of non-receptor TKs including Abl, Jak, Fak, Syk, Zap-70 and Csk. Inhibitors of Abl kinase are useful for the treatment of chronic myeloid leukemia (CML) as evidenced by STI-571, marketed as Gleevec [Kantarjian, H., *N. Engl. J. Med.*, 346 (9), 645 (2001)]. Compounds that inhibit both Abl and Src tyrosine kinases may also be useful for the treatment of CML [Warmuth, *Curr. Pharm. Design,* 9, 2043 (2003)].

Two members of the cytoplasmic protein TKs, lck and ZAP-70 are predominately expressed on T-cells and natural killer (NK) cells. Inhibitors of these kinases can suppress the immune system and therefore have possible therapeutic potential to treat autoimmune diseases such as rheumatoid arthritis, sepsis, and transplant rejection [Kamens, J. S., *Current Opin. Investig. Drugs,* 2, 1213 (2001); Myers, M., *Current Pharm. Design,* 3, 473 (1997)]. A low molecular weight Lck inhibitor is effective in preventing allograft rejection [Waegell, W. *Transplant. Proceed.* 34. 1411 (2002).

Besides TKs, there are additional kinases including those that phosphorylate serine and/or threonine residues on proteins. A major pathway in the cellular signal transduction cascade is the mitogen-activated protein kinase (MAPK) pathway which consists of the MAP kinase kinases (MAPKK), including mek, and their substrates, the MAP kinases (MAPK), including erk [Seger, R., *FASEB,* 9, 726 (1995)]. When activated by phosphorylation on two serine residues by upstream kinases, such as members of the raf family, mek catalyzes the phosphorylation of threonine and tyrosine residues on erk. The activated erk then phosphorylates and activates both transcription factors in the nucleus and other cellular targets. Over-expression and/or over-activation of mek or erk is associated with various human cancers [Sivaraman, V. S., *J. Clin. Invest.,* 99, 1478 (1997)].

As mentioned above, members of the raf family of kinases phosphorylate serine residues on mek. There are three serine/threonine kinase members of the raf family known as a-raf, b-raf and c-raf. While mutations in the raf genes are rare in human cancers, c-raf is activated by the ras oncogene which is mutated in a wide number of human tumors. Therefore inhibition of the kinase activity of c-raf may provide a way to prevent ras mediated tumor growth [Campbell, S. L., *Oncogene,* 17, 1395 (1998)].

The cyclin-dependent kinases (cdks), including cdc2/cyclin B, cdk2/cyclin A, cdk2/cyclin E and cdk4/cyclin D, and others, are serine/threonine kinases that regulate mammalian cell division. Increased activity or activation of these kinases is associated with the development of human tumors [Garrett, M. D., *Current Opin. Genetics Devel.,* 9, 104 (1999); Webster, K. R., *Exp. Opin. Invest. Drugs,* 7, 865 (1998)]. Additional serine/threonine kinases include PDK1, SGK and the protein kinases A, B, and C, known as PKA or cyclic AMP-dependent protein kinase, PKB (Akt), and PKC, all of which play key roles in signal transduction pathways responsible for oncogenesis [Glazer, R. I., *Current Pharm. Design,* 4(3), 277 (1998)]. Compounds capable of inhibiting the kinase activity of mek, erk, raf, cdc2/cyclin B, cdk2/cyclin A, cdk2/cyclin E, cdk4/cyclin D, PDK1, SGK, PKA, PKB (Akt) or PKC may be useful in the treatment of diseases characterized by abnormal cellular proliferation, such as cancer.

The serine/threonine kinase UL97 is a virion-associated protein kinase which is required for the replication of human cytomegalovirus [Wolf, D. G., *Arch. Virology* 143(6), 1223 (1998) and He, Z., *J. Virology,* 71, 405(1997)]. Compounds capable of inhibiting the kinase activity of UL97 may be useful antiviral therapeutics. Since certain bacteria require the action of a histidine kinase for proliferation [Loomis, W. F., *J. Cell Sci.,* 110, 1141 (1997)], compounds capable of inhibiting such histidine kinase activity may be useful antibacterial agents.

Other 4-(2,4-dichloro-5-methoxyphenyl)amino-7-furyl-3-quinolinecarbonitriles have been reported as kinase inhibitors. These compounds differ both in nature and placement of substituents at various positions when compared to the compounds of this invention. This invention relates to certain 4-(2,4-dichloro-5-methoxyphenyl) amino-7-furyl-6-methoxy-3-quinolinecarbonitriles as well as their pharmaceutically acceptable salts of Formula I. In these examples position 3 of the furan is attached to position 7 of the 3-quinolinecarbonitrile and position 5 of the furan is substituted by a methylamino group that contains various substituents on the amino group.

SUMMARY OF THE INVENTION

This invention relates to compounds having the structure of Formula I

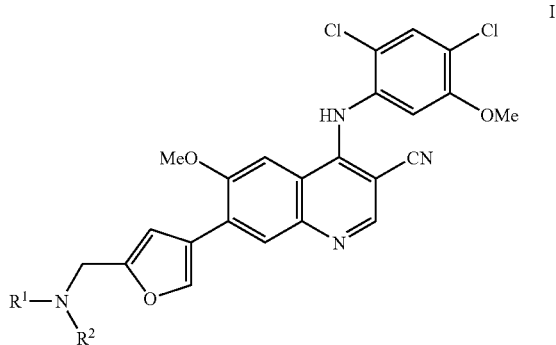

wherein:

$R^1$ and $R^2$ may be the same or different and are selected from H, alkyl of 1 to 6 carbon atoms, $(CH_2)_n XR^4$, $(CH_2)_n NZZ'$, alkenyl of 2-6 carbon atoms, alkynyl of 2-6 carbon atoms, aryl, or heteroaryl;

$R^1$ and $R^2$ can be taken together with the nitrogen to which they are attached to form a heterocyclic ring optionally having an additional heteroatom selected from nitrogen, oxygen, and sulfur, wherein the sulfur can be mono or di-oxidized, optionally substituted with at least one —$R^3$ on a carbon or nitrogen, or on nitrogen by a group —$(CH_2)_n XR^4$, —$(CH_2)_n NZZ'$, or on carbon by a group —$(CH_2)_q XR^4$, —$(CH_2)_q NZZ'$, halogen;

Z and Z' are selected from H, alkyl of 1 to 6 carbon atoms alkenyl of 2-6 carbon atoms, alkynyl of 2-6 carbon atoms, aryl, or heteroaryl; and Z and Z' can be taken together with the nitrogen to which they are attached to form a heterocyclic ring optionally containing an additional heteroatom selected from nitrogen, oxygen and sulfur;

$R^3$ is alkyl of 1 to 6 carbon atoms, alkenyl of 2-6 carbon atoms, alkynyl of 2-6 carbon atoms, oxygen, alkylaryl, alkylheteroaryl, cycloalkyl, aryl or heteroaryl; wherein the aryl or heteroaryl are optionally substituted with one or more alkyl of 1 to 6 carbon atoms, alkoxy of 1 to 6 carbon atoms, halogen, —OH, alkylhydroxy, or trifluoromethyl;

$R^4$ is H, alkyl of 1 to 6 carbon atoms, cis-alkenyl of 2-6 carbon atoms, trans-alkenyl of 2-6 carbon atoms, alkynyl of 2-6 carbon atoms, aryl or heteroaryl;

X is O, S, $NR^4$;

n is 2-5; and q is 0-5.

Compounds of the invention or a pharmaceutically acceptable salt thereof include:

4-[(2,4-dichloro-5-methoxyphenyl)amino]-6-methoxy-7-{5-[(4-methyl piperazin-1-yl)methyl]-3-furyl}-3-quinolinecarbonitrile;

4-[(2,4-dichloro-5-methoxyphenyl)amino]-7-{5-[(dimethylamino)methyl]-3-furyl}-3-quinolinecarbonitrile;

4-[(2,4-dichloro-5-methoxyphenyl)amino]-6-methoxy-7-[5-(morpholin-4-ylmethyl)]-3-furyl]-3-quinolinecarbonitrile;

4-[(2,4-dichloro-5-methoxyphenyl)amino]-6-methoxy-7-{5-[(4-phenylpiperazin-1-yl)methyl]-3-furyl}-3-quinolinecarbonitrile;

4-[(2,4-dichloro-5-methoxyphenyl)amino]-6-methoxy-7-(5-{[4-(2,4-dimethoxyphenyl)piperazin-1-yl]methyl}-3-furyl)-3-quinolinecarbonitrile;

4-[(2,4-dichloro-5-methoxyphenyl)amino]-6-methoxy-7-[5-(pyrrolidin-1-ylmethyl)-3-furyl]quinoline-3-carbonitrile, 4-[(2,4-dichloro-5-methoxyphenyl)amino]-6-methoxy-7-[5-(piperidin-1-ylmethyl)-3-furyl]quinoline-3-carbonitrile;

4-[(2,4-dichloro-5-methoxyphenyl)amino]-7-{5-[(diethylamino)methyl]-3-furyl}-6-methoxyquinoline-3-carbonitrile;

4-[(2,4-dichloro-5-methoxyphenyl)amino]-7-{5-[(4-ethylpiperazin-1-yl)methyl]-3-furyl}-6-methoxyquinoline-3-carbonitrile;

4-[(2,4-dichloro-5-methoxyphenyl)amino]-6-methoxy-7-(5-{[4-(1-methylpiperidin-4-yl)piperazin-1-yl]methyl}-3-furyl)quinoline-3-carbonitrile;

4-[(2,4-dichloro-5-methoxyphenyl)amino]-6-methoxy-7-{5-[(4-pyrrolidin-1-ylpiperidin-1-yl)methyl]-3-furyl}quinoline-3-carbonitrile;

7-{5-[(4-butylpiperazin-1-yl)methyl]-3-furyl}-4-[(2,4-dichloro-5-methoxyphenyl)amino]-6-methoxyquinoline-3-carbonitrile;

4-[(2,4-dichloro-5-methoxyphenyl)amino]-6-methoxy-7-(5-{[4-(2-morpholin-4-ylethyl)piperazin-1-yl]methyl}-3-furyl)quinoline-3-carbonitrile;

7-{5-[(4-benzylpiperazin-1-yl)methyl]-3-furyl}-4-[(2,4-dichloro-5-methoxyphenyl)amino]-6-methoxyquinoline-3-carbonitrile;

4-[(2,4-dichloro-5-methoxyphenyl)amino]-6-methoxy-7-(5-{[4-(2-phenylethyl)piperazin-1-yl]methyl}-3-furyl)quinoline-3-carbonitrile;

4-[(2,4-dichloro-5-methoxyphenyl)amino]-7-{5-[(dipropylamino)methyl]-3-furyl}-6-methoxyquinoline-3-carbonitrile;

4-[(2,4-dichloro-5-methoxyphenyl)amino]-7-{5-[(1,1-dioxidothiomorpholin-4-yl)methyl]-3-furyl}-6-methoxyquinoline-3-carbonitrile;

4-[(2,4-dichloro-5-methoxyphenyl)amino]-6-methoxy-7-{5-[(1-oxidothiomorpholin-4-yl)methyl]-3-furyl}quinoline-3-carbonitrile;

7-{5-[(4-cyclohexylpiperazin-1-yl)methyl]-3-furyl}-4-[(2,4-dichloro-5-methoxyphenyl)amino]-6-methoxyquinoline-3-carbonitrile;

4-[(2,4-dichloro-5-methoxyphenyl)amino]-6-methoxy-7-(5-{[4-(4-methoxyphenyl)piperazin-1-yl]methyl}-3-furyl)quinoline-3-carbonitrile;

4-[(2,4-dichloro-5-methoxyphenyl)amino]-6-methoxy-7-{5-[(4-pyridin-4-ylpiperazin-1-yl)methyl]-3-furyl}quinoline-3-carbonitrile;

4-[(2,4-dichloro-5-methoxyphenyl)amino]-6-methoxy-7-(5-{[4-(4-methylphenyl)piperazin-1-yl]methyl}-3-furyl)quinoline-3-carbonitrile;

7-(5-{[4-(4-chlorophenyl)piperazin-1-yl]methyl}-3-furyl)-4-[(2,4-dichloro-5-methoxyphenyl)amino]-6-methoxyquinoline-3-carbonitrile;

4-[(2,4-dichloro-5-methoxyphenyl)amino]-7-(5-{[4-(4-hydroxyphenyl)piperazin-1-yl]methyl}-3-furyl)-6-methoxyquinoline-3-carbonitrile;

4-[(2,4-dichloro-5-methoxyphenyl)amino]-6-methoxy-7-[5-({4-[4-(trifluoromethyl)phenyl]piperazin-1-yl}methyl)-3-furyl]quinoline-3-carbonitrile;

4-[(2,4-dichloro-5-methoxyphenyl)amino]-6-methoxy-7-[5-(thiomorpholin-4-ylmethyl)-3-furyl]quinoline-3-carbonitrile;

4-[(2,4-dichloro-5-methoxyphenyl)amino]-7-(5-{[[2-(dimethylamino)ethyl](methyl)amino]methyl}-3-furyl)-6-methoxyquinoline-3-carbonitrile;

4-[(2,4-dichloro-5-methoxyphenyl)amino]-7-{5-[(4-isopropylpiperazin-1-yl)methyl]-3-furyl}-6-methoxyquinoline-3-carbonitrile;

4-[(2,4-dichloro-5-methoxyphenyl)amino]-6-methoxy-7-{5-[(4-methyl-1,4-diazepan-1-yl)methyl]-3-furyl}quinoline-3-carbonitrile;

4-[(2,4-dichloro-5-methoxyphenyl)amino]-6-methoxy-7-(5-{[4-(2-methoxyethyl)piperazin-1-yl]methyl}-3-furyl)quinoline-3-carbonitrile;

4-[(2,4-dichloro-5-methoxyphenyl)amino]-7-(5-{[4-(2-hydroxyethyl)piperazin-1-yl]methyl}-3-furyl)-6-methoxyquinoline-3-carbonitrile;

4-[(2,4-dichloro-5-methoxyphenyl)amino]-6-methoxy-7-(5-{[(2-methoxyethyl)(methyl)amino]methyl}-3-furyl)quinoline-3-carbonitrile;

4-[(2,4-dichloro-5-methoxyphenyl)amino]-7-[5-({4-[3-(diethylamino)propyl]piperazin-1-yl}methyl)-3-furyl]-6-methoxyquinoline-3-carbonitrile;

4-[(2,4-dichloro-5-methoxyphenyl)amino]-6-methoxy-7-(5-{[4-(pyridin-4-ylmethyl)piperazin-1-yl]methyl}-3-furyl)quinoline-3-carbonitrile; and 4-[(2,4-dichloro-5-methoxyphenyl)amino]-7-(5-{[4-(2,6-dimethylphenyl)piperazin-1-yl]methyl}-3-furyl)-6-methoxyquinoline-3-carbonitrile.

A method of treating or inhibiting a pathological condition or disorder consisting of an increase in Src expression in a mammal comprising, providing to said mammal an effective amount of the compound of Formula I or a pharmaceutically acceptable salt thereof.

A process for preparing the compounds of Formula I comprising:
  a. adding the boronic acid of Formula 1 to a quinolinecarbonitrile of Formula 2 in the presence of a solvent and a catalyst to yield a compound of Formula 3;

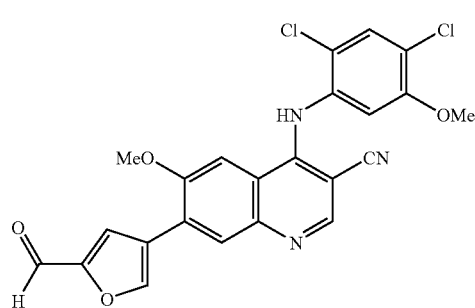

b. treating the compound of Formula 3 with an amine consisting of R¹R²NH to yield a compound of Formula I

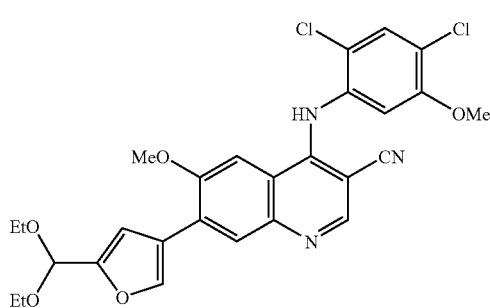

A process for preparing a compound of Formula 3 comprising:
  a. adding stannane of Formula 5 to the quinolinecarbonitrile of Formula 2 with a catalyst and solvent to yield a compound of Formula 6;

b. treating the compound of Formula 6 with an acid in a co-solvent to yield a compound of Formula 3:

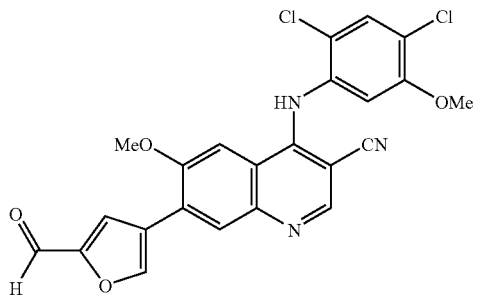

A process for preparing compounds of Formula I comprising:
  a. adding a boronic acid of Formula 7 to a quinolinecarbonitrile of Formula 3 to yield a compound of Formula I And where necessary converting the resultant compound of Formula I or another salt thereof, into a pharmaceutically acceptable salt thereof; or converting the resultant compound of Formula I into a further compound of Formula I; where the desired converting results in an optical isomer of Formula I.

A process for preparing 4,5-dibromo-2-furan carboxaldehyde comprising:
  a. cooling a solution of furfural in dibromomethane;
  b. adding aluminum tribromide to the solution in step (a);
  c. adding bromine to the completed reaction in step (b);
  d. stirring, quenching, and separating the product of step (c) to obtain 4,5-dibromo-2-furan carboxaldehyde.

The following experimental details are set forth to aid in an understanding of the invention, and are not intended, and should not be construed, to limit in any way the invention set forth in the claims that follow thereafter.

DETAILED DESCRIPTION OF THE INVENTION

This invention relates to compounds having the structure of Formula I

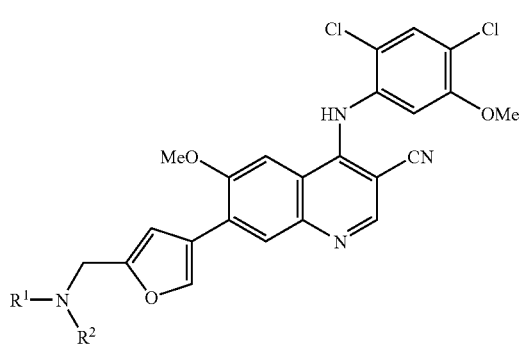

wherein:

$R^1$ and $R^2$ may be the same or different and are selected from H, alkyl of 1 to 6 carbon atoms, $(CH_2)_nXR^4$, $(CH_2)_nNZZ'$, alkenyl of 2-6 carbon atoms, alkynyl of 2-6 carbon atoms, aryl, or heteroaryl;

$R^1$ and $R^2$ can be taken together with the nitrogen to which they are attached to form a heterocyclic ring optionally having an additional heteroatom selected from nitrogen, oxygen, and sulfur, wherein the sulfur can be mono or di-oxidized, optionally substituted with at least one —$R^3$ on a carbon or nitrogen, or on nitrogen by a group —$(CH_2)_nXR^4$, —$(CH_2)_nNZZ'$, or on carbon by a group —$(CH_2)_qXR^4$, —$(CH_2)_qNZZ'$, halogen;

Z and Z' are selected from H, alkyl of 1 to 6 carbon atoms alkenyl of 2-6 carbon atoms, alkynyl of 2-6 carbon atoms, aryl, or heteroaryl; and Z and Z' can be taken together with the nitrogen to which they are attached to form a heterocyclic ring optionally containing an additional heteroatom selected from nitrogen, oxygen and sulfur;

$R^3$ is alkyl of 1 to 6 carbon atoms, alkenyl of 2-6 carbon atoms, alkynyl of 2-6 carbon atoms, oxygen, alkylaryl, alkylheteroaryl, cycloalkyl, aryl or heteroaryl; wherein the aryl or heteroaryl are optionally substituted with one or more alkyl of 1 to 6 carbon atoms, alkoxy of 1 to 6 carbon atoms, halogen, —OH, alkylhydroxy, or trifluoromethyl;

$R^4$ is H, alkyl of 1 to 6 carbon atoms, cis-alkenyl of 2-6 carbon atoms, trans-alkenyl of 2-6 carbon atoms, alkynyl of 2-6 carbon atoms, aryl or heteroaryl;

X is O, S, $NR^4$;

n is 2-5; and q is 0-5.

The terms used in this specification generally have their ordinary meanings in the art, within the context of the invention, and in the specific context where each term is used. Certain terms are discussed below, or elsewhere in the specification, to provide additional guidance to the practitioner in describing the compounds, compositions, and methods of the invention and how to make and use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. The use of examples anywhere in this specification, including examples of any terms discussed herein, is illustrative only, and in no way limits the scope and meaning of the invention or of any exemplified term. Likewise, the invention is not limited to the examples presented.

In addition to the utilities, described herein some of the compounds of this invention are intermediates useful for the preparation of other compounds of this invention.

As used herein, "about" or "approximately" shall generally mean within 20 percent, preferably within 10 percent, and more preferably within 5 percent of a given value or range.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

For purposes of this invention a heteroaryl is a heterocyclic ring. The heterocyclic ring is a five or six membered ring containing 1 to 4 heteroatoms selected from the group consisting of S, N, and O. The heteroaryl moieties include, but are not limited to, thiophene, furan, pyrrole, pyrazole, imidazole, 1,2,3-triazole, 1,2,4-triazole, tetrazole, thiazole, oxazole, isothiazole, isoxazole, 1,3,4-oxadiazole, 1,2,4-oxadiazole, 1,3,4-thiadiazole, pyridine, pyrimidine, pyrazine, pyridazine, 1,3,5-triazine, morpholine, thiomorpholine, piperidine, piperazine, pyrrolidine, tetrahydrothiophene, tetrahydrofuran, dioxane, 1,3-dioxolane, tetrahydropyran, The heteroaryl may be optionally substituted on a carbon, nitrogen, or sulfur.

For purposes of this invention "alkyl" includes both straight and branched alkyl moieties, preferably of 1-6 carbon atoms and includes iso-propyl, n-butyl and the like.

For purposes of this invention the term "cycloalkyl" refers to alicyclic hydrocarbon groups of 3-7 carbon atoms and includes a simple carbocycle as well as a carbocycle containing an alkyl substituent, for example, cyclopropyl, cyclohexyl, adamantyl and the like.

For purposes of this invention the term "aryl" is defined as an aromatic hydrocarbon moiety and may be substituted or unsubstituted. An aryl may be selected from but not limited to, the group: phenyl or biphenyl and may be optionally mono-, di-, tri- or tetra-substituted with substituents selected from, but not limited to, the group consisting of alkyl, acyl, alkoxycarbonyl, alkoxy, alkoxyalkyl, alkoxyalkoxy, cyano, halogen, hydroxy, or nitro.

For purposes of this invention "alkenyl" is defined as a radical aliphatic hydrocarbon that contains at least one carbon-carbon double bond and includes both straight and branched carbon chains of 2-6 carbon atoms in all possible configurational isomers, for example cis and trans.

For purposes of this invention "alkynyl" includes both straight or branched carbon chain of 2-6 carbon atoms that contains at least one carbon-carbon triple bond and includes propenyl and the like.

In one embodiment of this invention the alkyl, alkenyl and alkynyl groups can be substituted with such substituents as phenyl, substituted phenyl, hydroxy, halogen, alkoxy, thioalkyl, carboxy, alkoxycarbonyl and acyl.

For purposes of this invention "alkoxy" comprises a group of 1-6 carbon atoms having an alkyl group attached to an oxygen atom.

The compounds of this invention may include a "divalent group" defined herein as a linking group, for example, $CH_2CH_2$.

The compounds of this invention may contain one or more asymmetric carbon atoms and may thus give rise to stereoisomers, such as enantiomers and diastereomers. While shown without respect to stereochemistry in Formula I of the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center. Some of the compounds of this invention may contain one or more double bonds; in such cases, the compounds of this invention include each of the possible configurational isomers as well as mixtures of these isomers.

The compounds of this invention may include a halogen which includes the groups Cl, F, Br, I.

Compounds of Formula I may be pharmaceutically acceptable salts and with an acidic moiety can be formed from organic and inorganic bases. For example alkali metal salts: sodium, lithium, or potassium and N-tetraalkylammonium salts such as N-tetrabutylammonium salts. Similarly, when a compound of this invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

As used herein, the term "substituted" is contemplated to include all permissible substituents of organic compounds. In a broad aspect, the permissible substituents of organic compounds include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds. In one embodiment of this invention the alkyl, alkenyl and alkynyl groups can be substituted with such substituents as phenyl, substituted phenyl, hydroxy, halogen, alkoxy, thioalkyl, carboxy, alkoxycarbonyl and acyl. Substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

For purposes of this invention a solvent is used in performance of the reactions presented herein. Examples of solvents include but are not limited to ethylene glycol dimethyl ether, saturated sodium bicarbonate, dioxane, ethyl acetate, and aqueous sodium carbonate.

For purposes of this invention an elevated temperature is a temperature of about 50° C. to about 150° C.

For purposes of this invention a catalyst is selected from but not limited to a palladium catalyst.

In another embodiment, the present invention provides a method for the treatment of a pathological condition or disorder in a mammal. The present invention accordingly provides to a mammal, a pharmaceutical composition that comprises a compound of this invention in combination or association with a pharmaceutically acceptable carrier. The compound of this invention may be provided alone or in combination with other therapeutically effective compounds or therapies for the treatment or prevention of a pathological condition or disorder in a mammal.

The terms "prevent" or "prevention", as used herein, refer to the partial or complete inhibition of the development of a condition that impairs the performance of a function of the human body. The terms "treat" or "treatment", as used herein, refer to an attempt to ameliorate a disease problem. Further, the term "suppress" or "suppression" refers to a complete or partial inhibition of a condition, e.g., as evidenced by a lessening of the severity of the symptoms associated with that condition.

The compounds are preferably provided orally or subcutaneously. The compounds may be provided by intralesional, intraperitoneal, intramuscular or intravenous injection; infusion; liposome-mediated delivery; topical; nasal; anal; vaginal; sublingual; uretheral; transdermal; intrathecal; ocular; or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 1 g/kg or preferably at a dose range of 0.1 to 100 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage is the effective amount to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different pharmaceutical carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multi-lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of treating or inhibiting a pathological condition or disorder.

The compound of the present invention may be delivered locally via a capsule that allows a sustained release of the compound over a period of time. Controlled or sustained release compositions include formulation in lipophilic depots (for example, fatty acids, waxes, oils).

For purposes of this invention a pathological condition or disorder is linked to kinase molecules and inhibition of the signals generated by these molecules. Generated signals regulate a number of cellular functions such as cell growth, differentiation and cell death. The signals generated by these molecules have been implicated in initiation of tissue level responses, discussed in detail in the "Background of the Invention". The tissue level response triggers cellular damage or deregulated cellular growth. Deregulated cell growth occurs as a result of perturbed signals that moderate or alter cellular behavior or function. One method of treating a pathological condition or disorder would be to intercept the generated signal before it reaches the tissue. As described in detail previously specific kinases are associated with cellular events that have been implicated in pathological conditions or disorders including, but not limited to, cancer, stroke, osteoporosis, polycystic kidney disease, autoimmune disease, rheumatoid arthritis, neuropathic pain, and transplant rejection.

For purposes of this invention cancer is a cellular tumor. The natural course of the cancer is fatal. Metastasis develops as a result of adhesion of tumor cells to the vascular endothelium. As the tumor grows, cells are shed in the circulation and spawn an independent tumor nodule known as a metastasis.

For purposes of this invention the dose provided to a patient will vary depending upon what is being administered, the purpose of the administration, the manner of administration, and the like. A "therapeutically effective amount" is an amount sufficient to cure or ameliorate symptoms of cancer.

Throughout this application structures are presented with chemical names. Where any question arises as to nomenclature the structure prevails.

The compounds of this invention were prepared according to the following schemes: (1) from commercially available starting materials or: (2) from known starting materials which can be prepared as described in literature procedures or: (3) from new intermediates described in the schemes and experimental procedures. Optically active isomers may be prepared, for example, by resolving racemic derivatives or by asymmetric synthesis. The resolution can be carried out by methods known to those skilled in the art such as in the presence of a resolving agent, by chromatography, or combinations thereof.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art. Reactions are run under inert atmospheres where appropriate.

The preparation of the compounds and intermediates of this invention encompassed by Formula I is described as follows.

As shown in Scheme 1, addition of boronic acid of Formula 1 to a 3-quinolinecarbonitrile of Formula 2, provides the 3-quinolinecarbonitrile of Formula 3. This reaction is performed at elevated temperature in a solvent such as ethylene glycol dimethyl ether and saturated sodium bicarbonate in the presence of a palladium catalyst, preferentially tetrakis(triphenylphosphine)pallidium (0). Treatment of the compound of Formula 3 with an amine of Formula 4, $R^1R^2NH$, in the presence of a reducing agent, preferably sodium triacetoxyborohydride, in a solvent system that includes dichloromethane and N,N-dimethylformamide or 1-methyl-2-pyrrolidinone, optionally in the presence of acetic acid, provides compounds of Formula I.

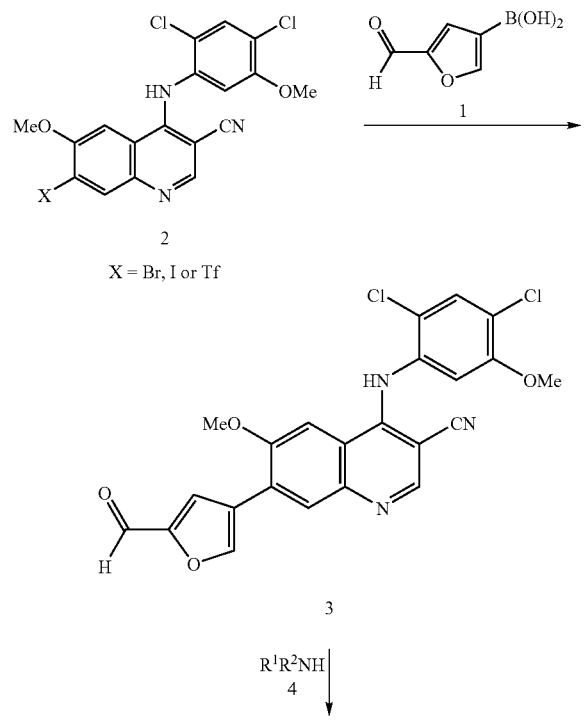

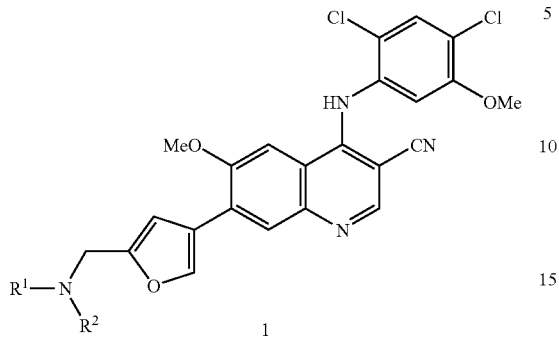

An alternate route to the key aldehyde intermediate 3 is shown in Scheme 2. Addition of the stannane of Formula 5 to a 3-quinolinecarbonitrile of Formula 2, provides the 3-quinolinecarbonitrile of Formula 6. This reaction is run at elevated temperature, preferably reflux temperature in dioxane in the presence of a palladium catalyst, preferably dichlorobis(triphenylphosphine)palladium (II). Treating of the diethylacetal group of 6 with an acid such as hydrochloric acid in a co-solvent such as tetrahydrofuran, provides the aldehyde intermediate 3. Other acetal protecting groups can also be used including 1,3-dioxolane and the like.

Scheme 3 shows another route to compounds of Formula I. Addition of a boronic acid of Formula 7 to a 3-quinolinecarbonitrile of Formula 2, provides the compounds of Formula I. This reaction is performed in a solvent such as ethylene glycol dimethyl ether and aqueous sodium carbonate in the presence of a palladium catalyst, for example [1,1'-bis(diphenylphosphino)ferrocene]dichloro-palladium (1:1) complex with $CH_2Cl_2$

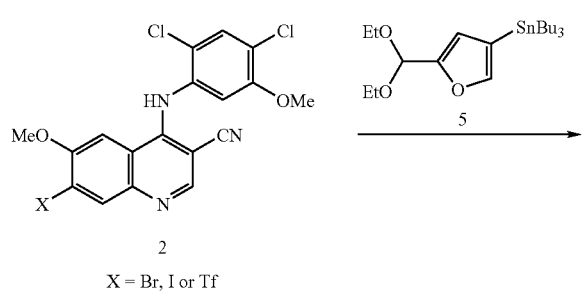

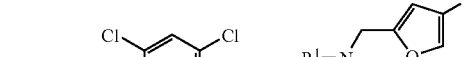

Scheme 4 shows another route to prepare compounds of Formula I.

Scheme 4

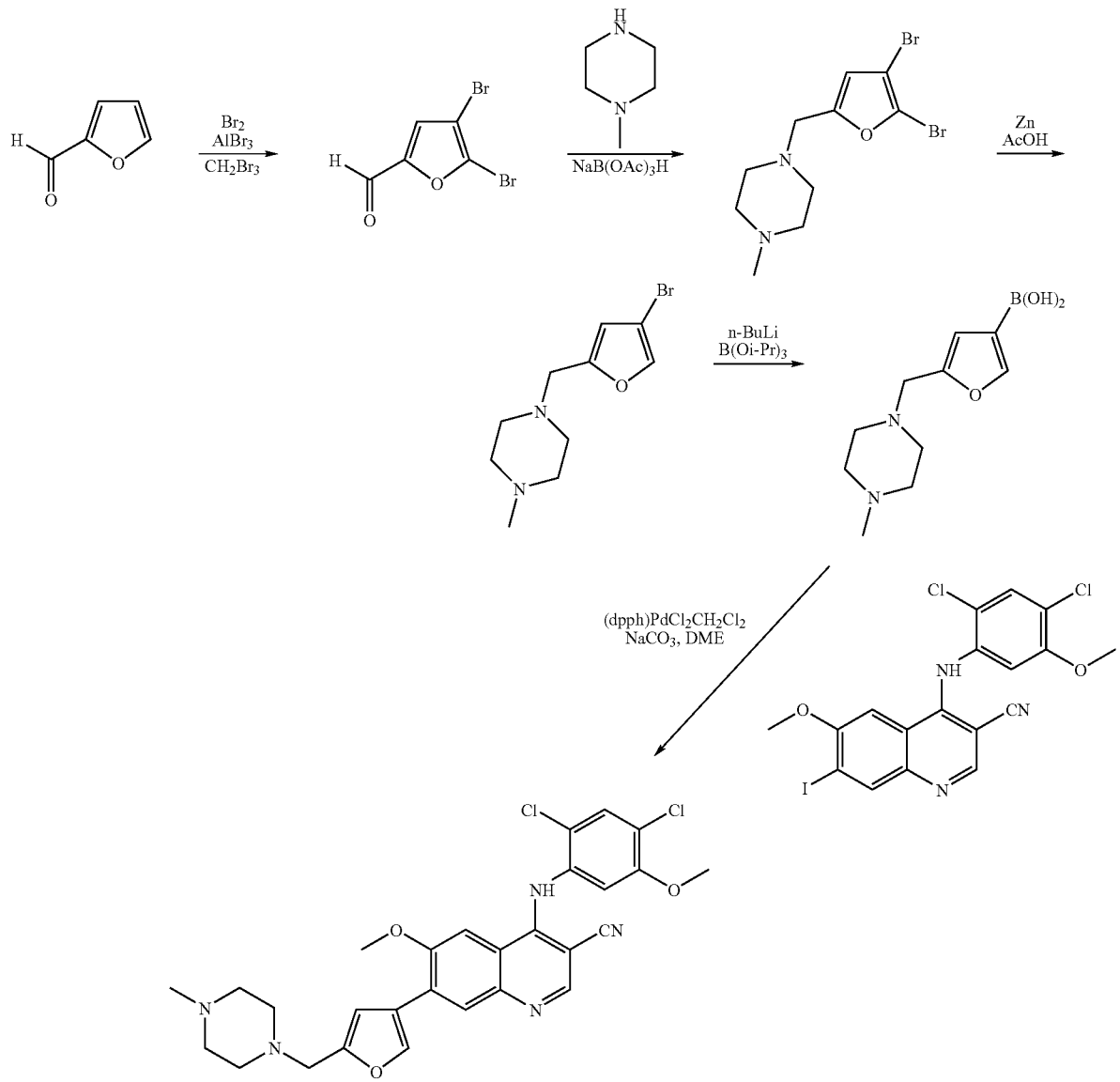

REFERENCE EXAMPLE 1

4-[(2,4-Dichloro-5-methoxyphenyl)amino]-7-(5-formyl-3-furyl)-6-methoxy-3-quinolinecarbonitrile A mixture of 3-cyano-4-(2,4-dichloro-5-methoxyanilino)-6-methoxy-7-quinolinyl trifluoromethanesulfonate (835 mg, 1.60 mmol), 2-formyl-4-furan boronic acid (446 mg, 3.21 mmol), and tetrakis(triphenylphosphine)pallidium (0) (20 mg) in 40 mL of ethylene glycol dimethyl ether and 25 mL of saturated aqueous sodium bicarbonate is heated at reflux for 3 hours and then cooled to room temperature. The reaction mixture is partitioned between dichloromethane and water. The aqueous layer is extracted with 10% methanol in ethyl acetate. The organic layers are combined, dried over magnesium sulfate, filtered and concentrated in vacuo. Diethyl ether is added to the residue and the solid is collected by filtration to provide 723 mg of 4-[(2,4-dichloro-5-methoxyphenyl) amino]-7-(5-formyl-3-furyl)-6-methoxy-3-quinolinecarbonitrile as a light yellow solid, mp 238-241° C.; $^1$H NMR (DMSO-$d_6$) δ 3.88 (s, 3H), 4.09 (s, 3H), 7.38 (s, 1H), 7.76 (s, 1H), 8.01 (s, 1H), 8.29 (broad s, 2H), 8.48 (s, 1H), 8.77 (s, 1H), 9.71 (s, 1H), 9.87 (s, 1H); MS 468.0, 470.0 (M+H)+; HRMS calcd: 468.05124, found: 468.0511 (M+H)+.

ALTERNATIVE PREPARATION OF REFERENCE EXAMPLE 1

4-[(2,4-Dichloro-5-methoxyphenyl)amino]-7-(5-formyl-3-furyl)-6-methoxy-3-quinolinecarbonitrile To a suspension of 4-[(2,4-dichloro-5-methoxyphenyl) amino]-7-[5-(diethoxymethyl)-3-furyl]-6-methoxy-3-quinolinecarbonitrile (2.60 g, 4.79 mmol) in 70 mL of tetrahydrofuran is added 27 mL of 2N hydrochloric acid. The mixture is stirred at room temperature for 1.5 hours then slowly added to 200 mL of saturated aqueous sodium bicarbonate. The mixture is stirred for 30 minutes and the solid is collected by filtration washing with water and ethyl acetate. The solid is heated with ethyl acetate and the suspension is filtered to provide 1.23 g of 4-[(2,4-dichloro-5-methoxyphenyl)amino]-7-(5-formyl-3-furyl)-6-methoxy-3-quinolinecarbonitrile.

REFERENCE EXAMPLE 2

4-[(2,4-Dichloro-5-methoxyphenyl)amino]-7-[5-(diethoxymethyl)-3-furyl]-6-methoxy-3-quinolinecarbonitrile A mixture of 4-(2,4-dichloro-5-methoxyanilino)-7-iodo-6-methoxy-3-quinolinecarbonitrile (3.5 g, 7.00 mmol), tributyl [5-(diethoxymethyl)-3-furanyl]stannane (generated from reaction of 4-bromo-2-(diethoxymethyl)-furan [ref. Chiarello, J, Joullie, M. M., Tetrahedron, 44(1), 41-48 (1988)] with tributyl tin chloride in the presence of n-BuLi) (5.76 g, 12.55 mmol), and dichlorobis(triphenylphosphine)pallidium (II) (100 mg) in 80 mL of dioxane is heated at reflux for 5 hours. Additional dichlorobis(triphenylphosphine)pallidium (II) (100 mg) is added and the reaction mixture is heated at reflux overnight. The reaction mixture is partitioned between ethyl acetate and water. The insoluble material is collected by filtration to provide 1.09 g of 4-[(2,4-dichloro-5-methoxyphenyl)amino]-7-[5-(diethoxymethyl)-3-furyl]-6-methoxy-3-quinolinecarbonitrile as a pale green solid; $^1$H NMR (DMSO-d$_6$) δ 1.18 (t, J=7 Hz, 6H), 3.63 (q, J=7 Hz, 4H), 3.87 (s, 3H), 4.07 (s, 3H), 5.60 (s, 1H), 7.13 (s, 1H), 7.37 (s, 1H), 7.76 (s, 1H), 7.95 (s, 1H), 8.15 (s, 1H), 8.35 (s, 1H), 8.45 (s, 1H), 9.84 (s, 1H); MS 542.1, 544.1 (M+H)+.

REFERENCE EXAMPLE 3

4,5-Dibromo-2-furancarboxaldehyde

A solution of furfural (81.9 g, 0.85 mole) in 170 mL of dibromomethane is cooled to 5° C. To this stirred solution is added over a period of 1.5 hours, aluminum tribromide (500 g, 1.87 moles) while maintaining the temperature below 15° C. Upon completion of this addition, bromine (272 g, 1.70 moles) is added over a period of one hour. The reaction mixture is stirred for 18 hours at room temperature. The reaction is then quenched with 2 L of an ice/water mixture. The mixture is filtered and organic phase is separated, diluted with 2 L of heptane and washed with a saturated aqueous solution of sodium thiosulfate followed by a wash with brine. The organic solution is dried over anhydrous magnesium sulfate. Filtration of the drying agent followed by solvent removal under vacuum gives 162.5 g (75% yield) of product as a red oil. $^1$H NMR of this product is consistent with the structure. Mass Spectrum indicates there is no chlorine present in the product.

Previous reports [eg Divald, Chun & Joullie, J. Org Chem, 41(17), 2835-2841 (1976)] on the synthesis of this material used AlCl$_3$ as catalyst. We have found that use of this catalyst generates small amounts of chlorine-substituted by-products. The use of AlBr$_3$ eliminates chlorinated by-products.

REFERENCE EXAMPLE 4

2-(4-Methylpiperazin-1-yl)-methyl]-4,5-dibromofuran

To a solution of 4,5-dibromo-2-furancarboxaldehyde (10.2 g, 0.0402 mole) in 20 mL of tetrahydrofuran is added 1-methylpiperazine while maintaining the temperature below 5° C. To this stirred solution is added sodium triacetoxyborohydride (12.7 g, 0.0599 mole) in three portions while maintaining the reaction temperature below 15° C. Acetic acid (1.2 g, 0.020 mole) is added and the resulting mixture is stirred for 18 hours at room temperature. The reaction is then quenched with 28 mL of water and made basic with the addition of 10 N sodium hydroxide. The solution is extracted with two 100 mL portions of methyl tert-butyl ether. The ether extracts are combined, filtered through solka floc and dried over dried over anhydrous magnesium sulfate. Filtration of the drying agent followed by solvent removal under vacuum gives 10.2 g (75% yield) of crude product as an off white solid. Recrystallization of the crude product from Heptane gives 8.1 g (60% recovery) of purified product as an off white solid with mp 74-75° C. $^1$H NMR of this product is consistent with the structure. Mass Spectrum indicates there is no chlorine present in the product.

REFERENCE EXAMPLE 5

2-(4-Methylpiperazin-1-yl)-methyl]-4-bromofuran

A stirred solution of 2-(4-methylpiperazin-1-yl)-methyl]-4,5-dibromofuran (199.6 g, 0.590 mole) in 450 mL of water and 189 mL (177.3 g, 2.95 moles) acetic acid is heated to 75° C. To this solution is added zinc powder (115.8 g, 1.77 moles) in three portions at 45-minute intervals. Heating at 75° C. is continued for an additional 5 hours then the mixture is cooled to room temperature and 300 mL of water is added. The mixture is cooled to below 1° C. and to it is added, dropwise over one hour, 800 mL of concentrated aqueous ammonium hydroxide. The solution is extracted with two 450 mL portions of methyl tert-butyl ether. The ether extracts are combined, filtered through solka floc and dried over anhydrous magnesium sulfate. Filtration of the drying agent followed by solvent removal under vacuum gives 148.6 g (97% yield) of product as a slightly yellow oil. $^1$H NMR and mass spectrum of this product are consistent with the structure.

EXAMPLE 1

4-[(2,4-Dichloro-5-methoxyphenyl)amino]-6-methoxy-{7-[5-[(4-methylpiperazin-1-yl)methyl]-3-furyl}-3-quinolinecarbonitrile A mixture of 4-[(2,4-dichloro-5-methoxyphenyl)amino]-7-(5-formyl-3-furyl)-6-methoxy-3-quinolinecarbonitrile (200 mg, 0.43 mmol) and 0.24 mL of N-methylpiperazine (2.2 mmol) in 5 mL of dichloromethane and 1 mL of dimethylformamide is cooled to 0° C. Sodium triacetoxyborohydride (470 mg, 2.22 mmol) is added in portions followed by a few drops of acetic acid. The resulting mixture is stirred at 0° C. for 10 minutes then at room temperature for 5.5 hours. The mixture is partitioned between ethyl acetate and saturated aqueous sodium bicarbonate. The organic phase is dried over magnesium sulfate, filtered and concentrated in vacuo. The residue is purified by flash column chromatography eluting with a gradient of 10% methanol in ethyl acetate to 1% ammonium hydroxide in a 1:4 mixture of methanol and ethyl acetate to provide 120 mg (51%) of 4-[(2,4-dichloro-5-methoxyphenyl)amino]-6 methoxy-7-{5-[(4-methylpiperazin-1-yl)methyl]-3-furyl}-3-quinolinecarbonitrile as a light yellow solid, mp 179-181° C.; $^1$H NMR (DMSO-d$_6$) δ 2.15 (s, 3H), 2.23-2.36 (broad s, 4H), 2.38-2.49 (broad s, 4H), 3.54 (s, 2H), 3.87 (s, 3H), 4.06 (s, 3H), 7.01 (s, 1H), 7.33 (s, 1H), 7.74 (s, 1H), 7.94 (s, 1H), 8.10 (s, 1H), 8.28 (s, 1H), 8.43 (s, 1H), 9.82 (s, 1H); MS 552.1, 554.1 (M+H)+; HRMS calcd: 552.15638, found: 552.15599 (M+H)+.

Analysis for $C_{28}H_{27}Cl_2N_5O_3$-$0.25H_2O$: Calcd: C, 60.38; H, 4.98; N, 12.58. Found: C, 60.29; H, 4.81; N, 12.30.

ALTERNATIVE PREPARATION OF EXAMPLE 1

4-[(2,4-Dichloro-5-methoxyphenyl)amino]-6-methoxy-{7-[5-[(4-methylpiperazin-1-yl)methyl]-3-furyl}-3-quinolinecarbonitrile A stirred solution of 2-(4-methylpiperazin-1-yl)-methyl]-4-bromofuran (3.37 g, 0.0130 mole) and tri-isopropyl borate (4.15 g, 0.0221 mole) is cooled to −78° C. and at this temperature, 12.5 mL of a 1.35 molar solution of n-butyl lithium (0.0169 mole) is added over 10 minutes. The temperature is kept at −78° C. for 5 hours then allowed to rise to room temperature overnight. Water (1.6 mL) is added and the solvents are removed under vacuum. The sticky residue is suspended in 50 mL of dimethoxyethane and 4-(2,4-dichloro-5-methoxyanilino)-7-iodo-6-methoxy-3-quinolinecarbonitrile (5.0 g, 0.010 mol) and catalyst, (dppf)PdCl$_2$.CH$_2$Cl$_2$ (0.204 g, 0.00025 mole), are added. A solution of sodium carbonate (4.24 g, 0.040 mole) in 12 mL of water is added and the reaction mixture is heated to 80° C. for 1.5 hours. The reaction mixture is cooled to 0° C. and 60 mL of ethyl acetate and 100 mL of water are added. The aqueous phase is separated and extracted with 50 mL of ethyl acetate. The organic phases are combined, washed with brine and dried over anhydrous sodium sulfate. Filtration of the drying agent followed by solvent removal under vacuum gives 6.94 g of crude product. The crude product is dissolved in 45 mL of ethyl acetate and 0.250 g of Darco is added. The mixture is stirred for one hour and filtered through celite. The filtrate was extracted several times with 10% acetic acid in water. The aqueous acetic acid extracts are basified with concentrated aqueous ammonium hydroxide and extracted several times with ethyl acetate. The ethyl acetate extracts are combined and dried over anhydrous sodium sulfate. Filtration of the drying agent followed by solvent removal under vacuum gives 5.51 g of product (99% crude yield) as a yellow glassy solid. A 3.48 g portion of this solid was crystallized by dissolving it in 9 mL of acetone and allowing it to stand for a few minutes. Filtration afforded 2.54 g (73% yield) of purified product shown by HPLC to be >98% pure.

EXAMPLE 2

4-[(2,4-Dichloro-5-methoxyphenyl)amino]-6-methoxy-7-{5-[(dimethylamino)methyl]-3-furyl}-3-quinolinecarbonitrile Prepared according to the route used to prepare Example 1: mp 133-138° C.; $^1$H NMR (DMSO-d$_6$) δ 2.20 (s, 6H), 3.49 (s, 2H), 3.87 (s, 3H), 4.07 (s, 3H), 7.03 (s, 1H), 7.38 (s, 1H), 7.76 (s, 1H), 7.95 (s, 1H), 8.13 (s, 1H), 8.30 (s, 1H), 8.45 (s, 1H), 9.82 (s, 1H); MS 497.1, 499.1 (M+H)+; HRMS calcd: 497.11418, found: 497.11291 (M+H)+.

EXAMPLE 3

4-[(2,4-Dichloro-5-methoxyphenyl)amino]-6-methoxy-7-[5-(morpholin-4-ylmethyl)-3-furyl]-3-quinolinecarbonitrile Prepared according to the route used to prepare Example 1: mp 164-166° C.; $^1$H NMR (DMSO-d$_6$) δ 2.39-2.46 (broad s, 4H), 3.50-3.60 (complex m, 6H), 3.87 (s, 3H), 4.06 (s, 3H), 7.05 (s, 1H), 7.36 (s, 1H), 7.75 (s, 1H), 7.94 (s, 1H), 8.12 (s, 1H), 8.30 (s, 1H), 8.44 (s, 1H), 9.81 (s, 1H); MS 539.1, 541.1 (M+H)+.

Analysis for $C_{27}H_{24}Cl_2N_4O_4$-$0.50H_2O$: Calcd: C, 59.13; H, 4.60; N, 10.20. Found: C, 58.83; H, 4.46; N, 10.09.

EXAMPLE 4

4-[(2,4-Dichloro-5-methoxyphenyl)amino]-6-methoxy-7-{5-[(4-phenylpiperazin-1-yl)methyl]-3-furyl}-3-quinolinecarbonitrile Prepared according to the route used to prepare Example 1: mp 201-203° C.; $^1$H NMR (DMSO-d$_6$) δ2.52-2.62 (broad s, 4H), 3.09-3.19 (broad s, 4H), 3.34 (s, 2H), 3.87 (s, 3H), 4.07 (s, 3H), 6.77 (t, J=7 Hz, 1H), 6.92 (d, J=8 Hz, 2H), 7.09 (s, 1H), 7.20 (t, J=8 Hz, 2H), 7.38 (s, 1H), 7.76 (s, 1H), 7.95 (s, 1H), 8.14 (s, 1H), 8.32 (s, 1H), 8.45 (s, 1H), 9.83 (s, 1H); MS 614.1, 616.2 (M+H)+; HRMS calcd: 614.17203, found: 614.17153 (M+H)+.

EXAMPLE 5

4-[(2,4-Dichloro-5-methoxyphenyl)amino]-6-methoxy-7-(5-{[4-(2,4-dimethoxyphenyl)piperazin-1-yl]methyl}-3-furyl)-3-quinolinecarbonitrile Prepared according to the route used to prepare Example 1: mp 223-225° C.; $^1$H NMR (DMSO-d$_6$) δ2.51-2.61 (broad s, 4H), 2.82-2.92 (broad s, 4H), 3.63 (s, 2H), 3.69 (s, 3H), 3.74 (s, 3H), 3.87 (s, 3H), 4.07 (s, 3H), 6.42 (dd, J=8.5, 2.5 Hz, 1H), 6.51 (d, J=2.5 Hz, 1H), 6.81 (d, J=8.5 Hz, 1H), 7.07 (s, 1H), 7.38 (s, 1H), 7.76 (s, 1H), 7.95 (s, 1H), 8.14 (s, 1H), 8.32 (s, 1H), 8.45 (s, 1H), 9.84 (s, 1H); MS 337.5 (M+2H)+, 674.0 (M+H)+; HRMS calcd: 674.1931, found: 674.1944 (M+H)+.

Examples 6-35 were prepared according to the route used to prepare Example 1.

EXAMPLE 6

4-[(2,4-dichloro-5-methoxyphenyl)amino]-6-methoxy-7-[5-(pyrrolidin-1-ylmethyl)-3-furyl]quinoline-3-carbonitrile

MS (ES)+523.1

EXAMPLE 7

4-[(2,4-dichloro-5-methoxyphenyl)amino]-6-methoxy-7-[5-(piperidin-1-ylmethyl)-3-furyl]quinoline-3-carbonitrile

MS (ES)+537.1

EXAMPLE 8

4-[(2,4-dichloro-5-methoxyphenyl)amino]-7-{5-[(diethylamino)methyl]-3-furyl}-6-methoxyquinoline-3-carbonitrile

MS (ES)+525.5

EXAMPLE 9

4-[(2,4-dichloro-5-methoxyphenyl)amino]-7-{5-[(4-ethylpiperazin-1-yl)methyl]-3-furyl}-6-methoxyquinoline-3-carbonitrile

MS (ES)+566.1

EXAMPLE 10

4-[(2,4-dichloro-5-methoxyphenyl)amino]-6-methoxy-7-(5-{[4-(1-methylpiperidin-4-yl)piperazin-1-yl]methyl}-3-furyl)quinoline-3-carbonitrile

MS (ES)+635.2

EXAMPLE 11

4-[(2,4-dichloro-5-methoxyphenyl)amino]-6-methoxy-7-{5-[(4-pyrrolidin-1-ylpiperidin-1-yl)methyl]-3-furyl}quinoline-3-carbonitrile

MS (ES)+606.1

EXAMPLE 12

7-{5-[(4-butylpiperazin-1-yl)methyl]-3-furyl}-4-[(2,4-dichloro-5-methoxyphenyl)amino]-6-methoxyquinoline-3-carbonitrile

MS (ES)+594.5

EXAMPLE 13

4-[(2,4-dichloro-5-methoxyphenyl)amino]-6-methoxy-7-(5-{[4-(2-morpholin-4-ylethyl)piperazin-1-yl]methyl}-3-furyl)quinoline-3-carbonitrile

MS (ES)+651.1

EXAMPLE 14

7-{5-[(4-benzylpiperazin-1-yl)methyl]-3-furyl}-4-[(2,4-dichloro-5-methoxyphenyl)amino]-6-methoxyquinoline-3-carbonitrile

MS (ES)+628.7

EXAMPLE 15

4-[(2,4-dichloro-5-methoxyphenyl)amino]-6-methoxy-7-(5-{[4-(2-phenylethyl)piperazin-1-yl]methyl}-3-furyl)quinoline-3-carbonitrile

MS (ES)+642.1

EXAMPLE 16

4-[(2,4-dichloro-5-methoxyphenyl)amino]-7-{5-[(dipropylamino)methyl]-3-furyl}-6-methoxyquinoline-3-carbonitrile

MS (ES)+553.5

EXAMPLE 17

4-[(2,4-dichloro-5-methoxyphenyl)amino]-7-{5-[(1,1-dioxidothiomorpholin-4-yl)methyl]-3-furyl}-6-methoxyquinoline-3-carbonitrile

MS (ES)+587.5

EXAMPLE 18

4-[(2,4-dichloro-5-methoxyphenyl)amino]-6-methoxy-7-{5-[(1-oxidothiomorpholin-4-yl)methyl]-3-furyl}quinoline-3-carbonitrile

MS (ES)+571.5

EXAMPLE 19

7-{5-[(4-cyclohexylpiperazin-1-yl)methyl]-3-furyl}-4-[(2,4-dichloro-5-methoxyphenyl)amino]-6-methoxyquinoline-3-carbonitrile

MS (ES)+620.6

EXAMPLE 20

4-[(2,4-dichloro-5-methoxyphenyl)amino]-6-methoxy-7-(5-{[4-(4-methoxyphenyl)piperazin-1-yl]methyl}-3-furyl)quinoline-3-carbonitrile

MS (ES)+644.5

EXAMPLE 21

4-[(2,4-dichloro-5-methoxyphenyl)amino]-6-methoxy-7-[5-[(4-pyridin-4-ylpiperazin-1-yl)methyl]-3-furyl}quinoline-3-carbonitrile

MS (ES)+615.5

EXAMPLE 22

4-[(2,4-dichloro-5-methoxyphenyl)amino]-6-methoxy-7-(5-{[4-(4-methylphenyl)piperazin-1-yl]methyl}-3-furyl)quinoline-3-carbonitrile

MS (ES)+628.5

EXAMPLE 23

7-(5-{[4-(4-chlorophenyl)piperazin-1-yl]methyl}-3-furyl)-4-[(2,4-dichloro-5-methoxyphenyl)amino]-6-methoxyquinoline-3-carbonitrile

MS (ES)+650.5

EXAMPLE 24

4-[(2,4-dichloro-5-methoxyphenyl)amino]-7-(5-{[4-(4-hydroxyphenyl)piperazin-1-yl]methyl}-3-furyl)-6-methoxyquinoline-3-carbonitrile

MS (ES)+630.5

EXAMPLE 25

4-[(2,4-dichloro-5-methoxyphenyl)amino]-6-methoxy-7-[5-({4-[4-(trifluoromethyl)phenyl]piperazin-1-yl}methyl)-3-furyl]quinoline-3-carbonitrile

MS (ES)+682.5

EXAMPLE 26

4-[(2,4-dichloro-5-methoxyphenyl)amino]-6-methoxy-7-[5-(thiomorpholin-4-ylmethyl)-3-furyl]quinoline-3-carbonitrile

MS (ES)+555.5

EXAMPLE 27

4-[(2,4-dichloro-5-methoxyphenyl)amino]-7-(5-{[[2-(dimethylamino)ethyl](methyl)amino]methyl}-3-furyl)-6-methoxyquinoline-3-carbonitrile

MS (ES)+554.5

EXAMPLE 28

4-[(2,4-dichloro-5-methoxyphenyl)amino]-7-{5-[(4-isopropylpiperazin-1-yl)methyl]-3-furyl}-6-methoxyquinoline-3-carbonitrile

MS (ES)+580.5

EXAMPLE 29

4-[(2,4-dichloro-5-methoxyphenyl)amino]-6-methoxy-7-{5-[(4-methyl-1,4-diazepan-1-yl)methyl]-3-furyl}quinoline-3-carbonitrile

MS (ES)+566.5

EXAMPLE 30

4-[(2,4-dichloro-5-methoxyphenyl)amino]-6-methoxy-7-(5-{[4-(2-methoxyethyl)piperazin-1-yl]methyl}-3-furyl)quinoline-3-carbonitrile

MS (ES)+596.5

EXAMPLE 31

4-[(2,4-dichloro-5-methoxyphenyl)amino]-7-(5-{[4-(2-hydroxyethyl)piperazin-1-yl]methyl}-3-furyl)-6-methoxyquinoline-3-carbonitrile

MS (ES)+582.2

EXAMPLE 32

4-[(2,4-dichloro-5-methoxyphenyl)amino]-6-methoxy-7-(5-{[(2-methoxyethyl)(methyl)amino]methyl}-3-furyl)quinoline-3-carbonitrile

MS (ES)+541.5

EXAMPLE 33

4-[(2,4-dichloro-5-methoxyphenyl)amino]-7-[5-({4-[3-(diethylamino)propyl]piperazin-1-yl}methyl)-3-furyl]-6-methoxyquinoline-3-carbonitrile

MS (ES)+651.7

EXAMPLE 34

4-[(2,4-dichloro-5-methoxyphenyl)amino]-6-methoxy-7-(5-{[4-(pyridin-4-ylmethyl)piperazin-1-yl]methyl}-3-furyl)quinoline-3-carbonitrile

MS (ES)+629.2

EXAMPLE 35

4-[(2,4-dichloro-5-methoxyphenyl)amino]-7-(5-{[4-(2,6-dimethylphenyl)piperazin-1-yl]methyl}-3-furyl)-6-methoxyquinoline-3-carbonitrile

MS (ES)+642.3

The test procedures used and results obtained are shown below.

Src Kinase Assay

Recombinant human Src enzyme was obtained from PanVera (P3044). Biotinylated peptide corresponding to residues 6-20 of Cdk1 was used as a substrate (Biotin-KVEKIGEG-TYGVVYK-COOH). Homogeneous fluorescence resonance energy transfer kinase assays were performed using the europium/APC detection format (LANCE, Perkin Elmer). Src enzyme (10 ng) was mixed with biotinylated peptide (final concentration 2 µM), 50 mM Hepes (pH 7.5), 10 mM $MgCl_2$, 20 ug/ml BSA, 0.001% Brij-35 (Sigma), 100 µM ATP, 1% DMSO. The kinase reaction was incubated for 70 min at 37° C. The reaction was stopped with EDTA at a final concentration of 30 mM EDTA/25 mM Hepes (pH 7.5)/10 µg/ml BSA. The mixture was combined with Eu-labeled anti-phosphotyrosine antibody PT66 (Perkin Elmer, AD0068) and Streptavidin Surelight-APC (Perkin Elmer, CR130-100) in 50 mM Hepes (pH 7.5)/20 µg/ml BSA, and incubated for 30 min according to manufacturer's specifications. Fluorescence intensity at 665 nm was used to monitor the extent of the kinase reaction. Multiple entries for a given compound indicate that it was tested multiple times. The results obtained for representative compounds of this invention are listed in Table 1.

Anchorage Independent Src-transformed Fibroblast Proliferation Assay

Rat2 fibroblasts stably transformed with a plasmid containing a CMV promotor controlled v-Src/Hu c-Src fusion gene in which the catalytic domain of human c-Src was inserted in place of the v-Src catalytic domain in the v-Src gene are used for the measurement of src dependent suspension growth. Ultra-low cluster plates (Costar # 3474) are seeded with 10,000 cells per well on Day 1. Compound is added in serial two-fold dilutions from 10 micromolar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an $IC_{50}$ for proliferation (micromolar units) as follows: % inhibition= (Abs490 nm sample−blank)/(Abs490 nm no cmpd control−blank)×100%. The results obtained for representative compounds of this invention are listed in Table 1. Multiple entries for a given compound indicate that it was tested multiple times.

Anchorage Independent Lck-transformed Fibroblast Proliferation Assay

Rat2 fibroblasts stably transformed with a plasmid containing a CMV promotor controlled v-Src/Hu Lck fusion gene in which the catalytic domain of human Lck was inserted in place of the v-Src catalytic domain in the v-Src gene are used for the measurement of src dependent suspension growth. Ultra-low cluster plates (Costar # 3474) are seeded with 10,000 cells per well on Day 1. Compound is added in serial two-fold dilutions from 10 micromolar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an $IC_{50}$ for proliferation (micromolar units) as follows: % inhibition= (Abs490 nm sample−blank)/(Abs490 nm no cmpd control−blank)×100%. The results obtained for representative compounds of this invention are listed in Table 1. Multiple entries for a given compound indicate that it was tested multiple times.

TABLE 1

| Example | Src enzyme $IC_{50}$ nM | Src cells $IC_{50}$ nM | Lck cells $IC_{50}$ nM |
|---|---|---|---|
| 1 | 1.0, 0.6, 0.7, 0.8 | 7, 21, 16, 13, 16 | 12, 21, 27 |
| 2 | 0.7, 0.8 | 16, 13, 23, 29 | 11, 11 |
| 3 | 1.8, 1.2 | 25, 37 | 74, 110, 159 |
| 4 | 2.7, 4.9, 5.3, 2.7 | 32, 35 | 353, 447 |
| 5 | 3.5, 3.1 | 19, 17 | 246, 203, 239 |
| 6 | 0.8, 0.9 | | |
| 7 | 0.7, 0.7 | | |
| 8 | 0.9, 0.8 | | |
| 9 | 0.6, 0.7 | | |
| 10 | 0.5, 0.5 | | |
| 11 | 1.1, 1.0 | | |
| 12 | 2.5, 2.1 | | |
| 13 | 1.0, 1.0 | | |
| 14 | 33.7, 56.2 | | |
| 15 | 18.3, 13.3 | | |
| 16 | 10.2, 6.5 | | |
| 17 | 2.4, 2.1 | | |
| 18 | 1.5, 2.4 | | |
| 19 | 3.6, 2.8 | | |
| 20 | 10.0, 11.7 | | |
| 21 | 2.2, 1.9 | | |
| 22 | 12.8, 14.3 | | |
| 23 | 18.9, 17.0 | | |
| 24 | 6.0, 5.6 | | |
| 25 | 14.1, 14.4 | | |
| 26 | 9.1, 7.8 | | |
| 27 | 3.2, 2.5 | | |
| 28 | 1.0, 0.7 | | |
| 29 | 1.3, 1.0 | | |
| 30 | 1.9, 1.7 | | |
| 31 | 1.9, 1.8 | | |
| 32 | 2.9, 2.6 | | |
| 33 | 2.0, 2.0 | | |
| 34 | 2.5, 3.0 | | |
| 35 | 3.2, 5.6 | | |

Abl Kinase Assay

Wild type c-Abl was purchased from Panvera (P3049). Biotinylated peptide for the Abl kinase assay was obtained from Synpep (Biotin-NH-KEEEAIYMPFAKKK-COOH). Homogeneous fluorescence resonance energy transfer kinase assays were performed using the europium/APC detection format (LANCE, Perkin Elmer). Abl enzyme (2.5 ng c-Abl) was mixed with biotinylated peptide (final concentration 2 µM), 50 mM Hepes (pH 7.5), 10 mM $MgCl_2$, 20 ug/ml BSA, and 0.001% Brij-35 (Sigma). Compound was added with a final DMSO concentration of 1%, and incubated for ten minutes at 27° C. The kinase reaction was initiated by addition of ATP to a final concentration of 100 µM, and incubated for 30 minutes at 27° C. The reaction was stopped with EDTA at a final concentration of 30 mM EDTA/25 mM Hepes (pH 7.5)/10 µg/ml BSA. The mixture was combined with Eu-labeled phosphotyrosine antibody PT66 (Perkin Elmer, AD0068) and Streptavidin Surelight-APC (Perkin Elmer, CR130-100) in 50 mM Hepes (pH 7.5)/20 µg/ml BSA, and incubated for 30 minutes according to manufacturer's specifications. The reaction was monitored on a Wallac Victor with excitation at 340 nm and emission at 665 nm. Data was analyzed with the LSW data analysis plug-in for Excel (Microsoft).

The cell assays were performed as noted in Cancer Research 63, 375-381 (2003).

TABLE 2

| Example | c-Abl enzyme $IC_{50}$ nM | K562 Cells $IC_{50}$ nM | KU812 Cells $IC_{50}$ nM |
|---|---|---|---|
| 1 | 0.40, 0.40, 0.27, 0.25 | 5.6 | 6 |
| 2 | 0.37, 0.47 | | |
| 4 | 0.64, 0.65 | | |

HT29 Xenograft Assay

All animal studies were conducted under an approved Institutional Animal Care and Use Committee protocol. HT29 cells were suspended to 50 million cells/ml and 0.2 ml of the cell suspension was injected into 6-7 weeks old female nude mice (Charles River, Wilmington, Mass.). Tumors were staged on day 7 after which compound of Example 1 was administered once a day for 14 days by oral gavage at 100 mg/kg in 0.2 ml of 0.5% methocellulose and 0.4% Tween 80. At day 14 the T/C (growth of tumors in treated animals/growth of tumors in control animals) was 0.53.

Example 1 of this invention is a potent Src inhibitor: Enzyme $IC_{50}$=0.8 nM, Cell $IC_{50}$=15 nM. The importance of the 3,5 substitution on the furan is shown by the decreased activity seen with the corresponding 2,5 isomer: Enzyme $IC_{50}$=13 nM, Cell $IC_{50}$=550 nM. The importance of the 6-OMe substituent on the 3-quinolinecarbonitrile is shown by the decreased activity seen with the 6-H analog: Enzyme $IC_{50}$=3.2 nM, Cell $IC_{50}$=77 nM. The importance of the furan ring is shown by the decreased activity seen with the corresponding thiophene: Enzyme $IC_{50}$=3.7 nM pending, Cell $IC_{50}$=94 nM. Replacement of the N-Me-piperazine group of Example 1 with other amines also provided potent Src inhibitors, i.e. the dimethylamino analog, Example 2: Enzyme $IC_{50}$=0.8 nM, Cell $IC_{50}$=20 nM.

What is claimed is:

1. A compound of Formula I

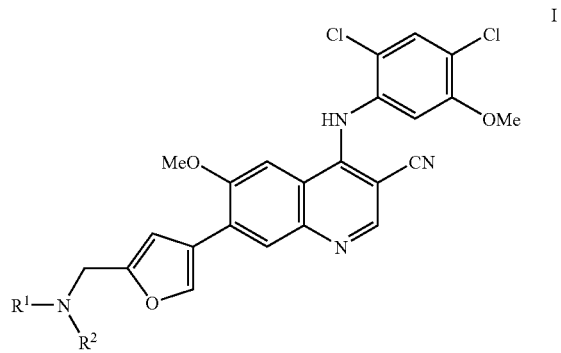

wherein:

R¹ and R² may be the same or different and are selected from H, alkyl of 1 to 6 carbon atoms, $(CH_2)_nXR^4$, $(CH_2)_nNZZ'$, alkenyl of 2-6 carbon atoms, alkynyl of 2-6 carbon atoms, aryl, or heteroaryl;

R¹ and R² can be taken together with the nitrogen to which they are attached to form a heterocyclic ring optionally having an additional heteroatom selected from nitrogen, oxygen, and sulfur, wherein the sulfur can be mono or di-oxidized, optionally substituted with at least one —R³ on a carbon or nitrogen, or on nitrogen by a group —$(CH_2)_nXR^4$, —$(CH_2)_nNZZ'$, or on carbon by a group —$(CH_2)_qXR^4$, —$(CH_2)_qNZZ'$, halogen Z and Z' are selected from H, alkyl of 1 to 6 carbon atoms alkenyl of 2-6 carbon atoms, alkynyl of 2-6 carbon atoms, aryl, or heteroaryl; and Z and Z' can be taken together with the nitrogen to which they are attached to form a heterocyclic ring optionally containing an additional heteroatom selected from nitrogen, oxygen and sulfur;

R³ is alkyl of 1 to 6 carbon atoms, alkenyl of 2-6 carbon atoms, alkynyl of 2-6 carbon atoms, oxygen, alkylaryl, alkylheteroaryl, cycloalkyl, aryl or heteroaryl, wherein the aryl or heteroaryl are optionally substituted with one or more alkyl of 1-6 carbon atoms, alkoxy of 1-6 carbon atoms, halogen, —OH, alkylhydroxy or trifluoromethyl;

R⁴ is H, alkyl of 1 to 6 carbon atoms, alkenyl of 2-6 carbon atoms, alkynyl of 2-6 carbon atoms, aryl or heteroaryl;

X is O, S, NR⁴;

n is 2-5;

q is 0-5; and pharmaceutically acceptable salts thereof.

2. A compound of Formula I

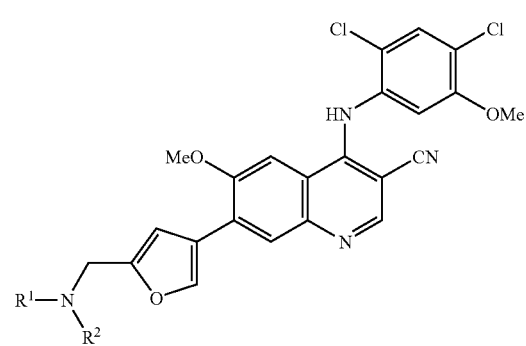

wherein:

R¹ and R² are alkyl of 1 to 3 carbon atoms;

R¹ and R² can be taken together with the nitrogen to which they are attached to form a heterocyclic ring which may have an additional heteroatom selected from nitrogen, oxygen, and sulfur, optionally substituted with —R³ on a carbon or a nitrogen or on nitrogen by a group —$(CH_2)_nNZZ'$;

Z and Z' taken together with the nitrogen to which they are attached may form a heterocyclic ring which may contain an additional heteroatom selected from nitrogen, oxygen and sulfur, optionally substituted with R³ on a C or N;

R³ is alkyl of 1 to 3 carbon atoms, alkylaryl, alkylheteroaryl, cycloalkyl, aryl, heteroaryl, wherein the aryl and heteroaryl may be optionally substituted with alkyl, alkoxy; and n is 2 to 3.

3. A compound of Formula I

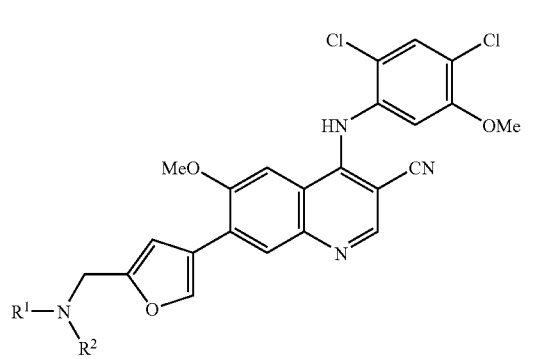

wherein:

R¹ and R² are an alkyl of 1 to 3 carbon atoms;

R¹ and R² can be taken together with the nitrogen to which they are attached to form a heterocyclic ring which may have an additional heteroatom selected from nitrogen, oxygen, and sulfur, optionally substituted with —R³ on a carbon or a nitrogen; and R³ is alkyl of 1 to 3 carbon atoms, aryl optionally substituted with at least one of alkoxy.

4. The compound of claim 1 comprising 4-[(2,4-dichloro-5-methoxyphenyl)amino]-6-methoxy-7-{5-[(4-methylpiperazin-1-yl)methyl]-3-furyl}-3-quinolinecarbonitrile.

5. The compound of claim 1 comprising 4-[(2,4-dichloro-5-methoxyphenyl)amino]-7-{5-[(dimethylamino)methyl]-3-furyl}-3-quinolinecarbonitrile.

6. The compound of claim 1 comprising 44-[(2,4-dichloro-5-methoxyphenyl)amino]-6-methoxy-7-[5-( morpholin-4-ylmethyl)]-3-furyl]-3-quinolinecarbonitrile.

7. The compound of claim 1 comprising 4-[(2,4-dichlbro-5-methoxyphenyl)amino]-6-methoxy-7-{5-[(4-phenylpiperazin-1-yl)methyl]-3-furyl}-3-quinolinecarbonitrile.

8. The compound of claim 1 comprising 4-[(2,4-dichloro-5-methoxyphenyl)amino]-6-methoxy-7-(5-{[4-(2,4-dimethoxyphenyl)piperazin-1-yl]methyl}-3-furyl)-3-quinolinecarbonitrile.

9. The compound of claim 1 comprising 4-[(2,4-dichloro-5-methoxyphenyl)amino]-6-methoxy-7-[(5-(pyrrolidin-1-ylmethyl)-3-furyl]quinoline-3-carbonitrile.

10. The compound of claim 1 comprising 4-[(2,4-dichloro-5-methoxyphenyl)a mino]-6-rnetboxy-7-[5-(piperidin-1-ylmethyl)-3-furyl]quinoline-3-carbonitrile.

11. The compound of claim 1 comprising 4-[(2,4-dichloro-5-methoxyphenyl)amino]-7-(5-[(diethylamino)methyl]-3-furyl}-6-methoxyquinoline-3-carbonitrile.

12. The compound of claim 1 comprising 4-[(2,4-dichloro-5-methoxyphenyl)amino]-7-{5-[(4-ethylpiperazin-1-yl)methyl]-3-furyl}-6-methoxyquinoline-3-carbonitrile.

13. The compound of claim 1 comprising 4-[(2,4-dichloro-5-methoxyphenyl)amino]-6-methoxy-7-(5-{[4(1-methylpiperidin-4-yl)piperazin-1-yl]methyl}-3-furyl)quinoline-3-carbonitrile.

14. The compound of claim 1 comprising 4-[(2,4-dichlbro-5-methoxyphenyl)amino]-6-methoxy-7-{5-[(4-pyrrolidin-1-ylpiperidin-1-yl)methyl]-3-furyl}quinoline-3-carbonitrile.

15. The compound of claim 1 comprising 7-{5-[(4-butylpiperazin-1-yl)methyl]-3-furyl}-4-[(2,4-dichloro-5-methoxyphenyl) amino]-6-methoxyquinoline-3-carbonitrile.

16. The compound of claim 1 comprising 4-[(2,4-dichloro-5-methoxyphenyl)amino]-6-methoxy-7-(5-{[4-(2-morpholin-4-ylethyl)piperazin-1-yl]methyl}-3-furyl)quinoline-3-carbonitrile.

17. The compound of claim 1 comprising 7-{5-[(4-benzylpiperazsn-1-yl)methyl]-3-furyl}4-[(2,4-dichloro-5-methoxyphenyl)amino]-6-methoxyquinoline-3-carbonitrile.

18. The compound of claim 1 comprising 4-[(2,4-dichloro-5-methoxyphenyl)amino]-6-methoxy-7-(5-{[4-(2-phenylethyl)piperazin-1-yl]methyl}-3-furyl)quinoline-3-carbonitrile.

19. The compound of claim 1 comprising 4-[(2,4-dichloro-5-methoxyphenyl)amino]-7-{5-[(dipropylamino)methyl]-3-furyl}-6-methoxyquinoline-3-carbonitrile.

20. The compound of claim 1 comprising 4-[(2,4-dichloro-5-methoxyphenyl)amino]-7-{5-[(1,1-dioxidothiomorpholin-4-yl)methyl]-3-furyl}-6-methoxyquinoline-3-carbonitrile.

21. The compound of claim 1 comprising 4-[(2,4-dichloro-5-methoxyphenyl)amino]-6-methoxy-7-{5-[(1-oxidothiomorpholin-4-yl)methyl]-3-furyl}quinoline-3-carbonitrile.

22. The compound of claim 1 comprising 7-{5-[(4-cyclohexylpiperazin-1-yl)methyl]-3-furyl}-4-[(2,4-dichloro-5methoxyphenyl)amino]-6-methoxyquinoline-3-carbonitrile.

23. The compound of claim 1 comprising 4-[(2,4-dichloro-5-methoxyphenyl)a mino]-6-methoxy-7-(5-{[4-(4-methoxyphenyl)piperazin-1-yl]methyl}-3-furyl)quinoline-3-carbonitrile.

24. The compound of claim 1 comprising 4-[(2,4-dichloro-5-methoxyphenyl)amino]-6-methoxy-7-{5-[(4-pyridin-4-ylpiperazin-1-yl)methyl]-3-furyl}quinoline-3-carbonitrile.

25. The compound of claim 1 comprising 4-[(2,4-dichloro-5-methoxyphenyl)amino]-6-methoxy-7-(5-{[4-(4-methylphenyl)piperazin-1-yl]methyl}-3-furyl)quinoline-3-carbonitrile.

26. The compound of claim 1 comprising 7-(5-{[4-(4-chlorophenyl)piperazin-1-yl]methyl}-3-furyl)-4-[(2,4-dichloro-5-methoxyphenyi)amino]-6-methoxyquinoline-3-carbonitrile.

27. The compound of claim 1 comprising 4-[(2,4-dichloro-5-methoxyphenyl)amino]-7-(5-{[4-(4-hydroxyphenyl)piperazin-1-yl]methyl}-3-furyl)-6-methoxyquinoline-3-carbonitrile.

28. The compound of claim 1 comprising 4-[(2,4-dichloro-5-methoxyphenyl)amino]-6-methoxy-7-[5-({4-[4-(trifluoromethyl)phenyl]piperazin-1-yl}methyl)-3-furyl]quinoline-3-carbonitrile.

29. The compound of claim 1 comprising 4-[(2,4-dichloro-5-methoxyphenyl)amino]-6-methoxy-7-[5-(thiomorpholin-4-ylmethyl)-3-furyl]quinoline-3-carbonitrile.

30. The compound of claim 1 comprising 4-[(2,4-dichloro-5-methoxyphenyl)amino]-7-(5-{[[2-(dimethylamino)ethyl](methyl)amino]methyl}-3-furyl)-6-methoxyquinoline-3-carbonitrile.

31. The compound of claim 1 comprising 4-[(2,4-dichloro-5-methoxyphenyl)amino]-7-{5-[(4-isopropylpiperazin-1-yl)methyl]-3-furyl}-6-methoxyquinoline-3-carbonitrile.

32. The compound of claim 1 comprising 4-[(2,4-dichloro-5-methoxyphenyl)amino]-6-methoxy-7-{5-[(4-methyl-1,4-diazepan-1-yl)methyl]-3-furyl}quinoline-3-carbonitrile.

33. The compound of claim 1 comprising 4-[(2,4-dichloro-5-methoxyphenyl)amino]-6-methoxy-7-(5-{[4-(2-methoxyethyl)piperazin-1-yl]methyl}-3-furyl)quinoline-3-carbonitrile.

34. The compound of claim 1 comprising 4-[(2,4-dichloro-5-methoxyphenyl)amino]-7-(5-{[4-(2-hydroxyethyl)piperazin-1-yl]methyl}-3-furyl)-6-methoxyquinoline-3-carbonitrnle.

35. The compound of claim 1 comprising 4-[(2,4-dichloro-5-methoxyphenyl)amino]-7-(5-{[4-(2,6-dimethylphenyl)piperazin-1-yl]methyl}-3-furyl)-6-methoxyquinoline-3-carbonitrile.

36. The compound of claim 1 comprising 4-[(2,4-dichloro-5-methoxyphenyl)amino]-7-[5-({4-[3-(diethylamino)propyl]piperazin-1-yl}methyl)-3-furyl]-6-methoxyquinoline-3-carbonitrile.

37. The compound of claim 1 comprising 4-[(2,4-dichloro-5-methoxyphenyl)amino[-6-methoxy-7-(5-{[4-(pyridin-4-ylmethyl)piperazin-1-yl]methyl}-3-furyl)quinoline-3-carbonitrile.

38. The compound of claim 1 comprising 4-[(2,4-dichloro-5-methoxyphenyl)amino]-7-(5-{[4-(2,6-dimethylphenyl)piperazin-1-yl]methyl}-3-furyl)-6-methoxyquinoline-3-carbonitrile.

39. A pharmaceutical composition comprising a compound of claim 1 and a pharmaceutically acceptable carrier.

40. The pharmaceutical composition of claim 39 wherein the compound is selected from:

4-[(2,4-dichloro-5-methoxyphenyl)amino]-6-methoxy-7-{5-[(4-methylpiperazin-1-yl)methyl]-3-furyl}-3-quinolinecarbonitrile;

4-[(2,4-dichloro-5-methoxyphenyl)amino]-7-{5-[(dimethylamino)methyl]-3-furyl{-3-quinolinecarbonitrile;

4-[(2,4-dichloro-5-methoxyphenyl)amino]-6-methoxy-7-[5-(morpholin-4-ylmethyl)]-3-furyi]-3-quinolinecarbonitrile;

4-[(2,4-dichloro-5-methoxyphenyl)amino]-6-methoxy-7-{5-[(4-phenylpiperazin-1-yl)methyl]-3-furyl}-3-quinolinecarbonitrile;

4-[(2,4-dichloro-5-methoxyphenyl)amino]-6-methoxy-7-(5-{[4-(2,4-dimethoxyphenyl)piperazin-1-yl]methyl}-3-furyl)-3-quinolinecarbonitrile;

4-[(2,4-dichloro-5-methoxyphenyl)amino]-6-methoxy-7-[5-(pyrrolidin-1-ylmethyl)-3-furyl]quinoline-3-carbonitrile;

4-[(2,4-dichloro-5-methoxyphenyl)amino]-6-methoxy-7-[5-(piperidin-1-ylmethyl)-3-furyl]quinoline-3-carbonitrile;

4-[(2,4-dichloro-5-methoxyphenyl)amino]-7-{5-[(diethylamino)methyl]-3-furyl)-6-methoxyquinoline-3-carbonitrile;

4-[(2,4-dichloro-5-methoxyphenyl)amino]-7-{5-[(4-ethyipiperazin-1-yl)methyl]-3-furyl) -6-methoxyquinoline-3-carbonitriie;

4-[(2,4-dichloro-5-methoxyphenyl)amino]-6-methoxy-7-(5-{[4-(1-methylpiperidin-4-yl)piperazin-1-yl]methyl}-3-furyl)quinoline-3-carbonitrile;

4-[(2,4-dichloro-5-methoxyphenyl)amino]-6-methoxy-7-{5-[(4-pyrrolidin-1-ylpiperidin-1-yl)methyl]-3-furyl}quinoline-3-carbonitrile;

7-{5-[(4-butylpiperazin-1-yl)methyi]-3-furyl}-4-[(2,4-dichloro-5-methoxyphenyl)amino]-6-methoxyquinoline-3-carbonitrile;

4-[(2,4-dichloro-5-methoxyphenyl)amino]-6-methoxy-7-(5-{[4-(2-morpholin-4-ylethyl)piperazin-1-yl]methyl}-3-furyl)quinoline-3-carbonitrile;

7-{5-[(4-benzylpiperazin-1-yl)methyl]-3-furyl}-4-[(2,4-dichloro-5-methoxyphenyl)amino]-6-methoxyquinoline-3-carbonitrile;

4-[(2,4-dichloro-5-methoxyphenyl)amino]-6-methoxy-7-(5-{[4-(2-phenylethyl)piperazin-1-yl]methyl}-3-furyl)quinoiine-3-carbonitrile;

4-[(2,4-dichloro-5-methoxyphenyl)amino]-7-{5-[(dipropylamino)methyl]-3-furyl}-6-methoxyquinoline-3-carbonitrile;

4-[(2,4-dichloro-5-methoxyphenyl)amino]-7-{5-[(1,1-dioxidothiomorpholin-4-yl)methyi]-3-furyl}-6-methoxyquinoline-3-carbonitrile;

4-[(2,4-dichloro-5-methoxyphenyl)amino]-6-methoxy-7-{5-[(1-oxidothiomorpholin-4-yl)methyl]-3-furyl}quinoline-3-carbonitrite;

7-{5-[(4-cyclohexylpiperazin-1-yl)methyl]-3-furyl}-4-[(2,4-dichloro-5-methoxyphenyl)amino]-6-methoxyquinoline-3-carbonitrile;

4-[(2,4-dichloro-5-methoxyphenyl)amino]-6-methoxy-7-(5-{[4-(4-methoxyphenyl)piperazin-1-yl]methyl}-3-furyl)quinoline-3-carbonitrile;

4-[(2,4-dichloro-5-methoxyphenyl)amino]-6-methoxy-7-{5-[(4-pyridin-4-ylpiperazin-1-yl)methyl]-3-furyl}quinoline-3-carbonitrile;

4-[(2,4-dichloro-5-methoxyphenyl)amino]-6-methoxy-7-(5-{[4-(4-methylphenyl)piperazin-1-yl]methyl}-3-furyl)quinoline-3-carbonitrile;

7-(5-{[4-(4-chlorophenyl)piperazin-1-yl]methyl}-3-furyl)-4-[(2,4-dichloro-5-methoxyphenyl)amino]-6-methoxyquinoline-3-carbonitrile;

4-[(2,4-dichloro-5-methoxyphenyl)ammo]-7-(5-{[4-(4-hydroxyphenyl)piperazin-1-yl]methyl}-3-furyl)-6-methoxyquinoline-3-carbonitrile;

4-[(2,4-dichloro-5-methoxyphenyl)amino]-6-methoxy-7-[5-({4-[4-(trifluoromethyl)phenyl]piperazin-1-yl}methyl)-3-furyl]quinoline-3-carbonitrile;

4-[(2,4-dichloro-5-methoxyphenyl)amino]-6-methoxy-7-[5-(thiomorpholin-4-ylmethyl) -3-furyl]quinoline-3-carbonitrile;

4-[(2,4-dichloro-5-methoxyphenyl)amino]-7-(5-{[[2-(dimethylamino)ethyl](methyl)amino]methyl}-3-furyl)-6-methoxyquinoline-3-carbonitrile;

4-[(2,4-dichloro-5-methoxyphenyl)amino]-7-}5-[(4-isopropylpiperazin-1-yl)methyl]-3-furyl}-6-methoxyquinoline-3-carbonitrtle;

4-[(2,4-dichloro-5-methoxyphenyl)amino]-6-methoxy-7-{5-[(4-methyl-1,4-diazepan-1-yl)methyl]-3-furyl)quinoiine-3-carbonitrile;

4-[(2,4-dichloro-5-methoxyphenyl)amino]-6-methoxy-7-(5-{[4-(2-methoxyethyl)piperazin-1-yl]methyl}-3-furyl)quinoline-3-carbonitrile;

4-[(2,4-dichloro-5-methoxyphenyl)amino]-7-(5-{[4-{2-hydroxyethyl)piperazin-1-yl]methyl}-3-furyl)-6-methoxyquinoline-3-carbonitrile;

4-[(2,4-dichloro-5-methoxyphenyl)amino]-7-(5-{[4-(2,6-dimethyiphenyl)piperazin-1-yl]methyl}-3-furyl)-6-methoxyquinoline-3-carbonitrile;

4-[(2,4-dichloro-5-methoxyphenyl)amino]-7-[5-({4-[3-(diethylamino)propyl]piperazin-1-yl}methyl)-3-furyl]-6-methoxyquinoline-3-carbonitrile;

4-[(2,4-dichloro-5-methoxyphenyl)amino]-6-methoxy-7-(5-{[4-( pyridin-4-ylmethyl)piperazin-1-yl]methyl}-3-furyl)quinoline-3-carbonitrile; and 4-[(2,4-dichloro-5-methoxyphenyl)amino]-7-(5-{[4-(2,6-dimethyiphenyl)piperazin-1-yl]methyl}-3-furyl)-6-methoxyquinoline-3-carbonitrile.

* * * * *

UNITED STATES PATENT AND TRADEMARK OFFICE
CERTIFICATE OF CORRECTION

PATENT NO. : 7,479,561 B2  Page 1 of 1
APPLICATION NO. : 11/201705
DATED : January 20, 2009
INVENTOR(S) : Diane Harris Boschelli et al.

It is certified that error appears in the above-identified patent and that said Letters Patent is hereby corrected as shown below:

Column 30
Line 35  "44-" should be -- 4- --
Line 36  "5-( morpholin" should be -- 5-(morpholin --
Line 38  "2,4-dichlbro-" should be -- 2,4-dichloro- --
Line 49  ")a mino]" should be -- )amino] --
Line 49  "6-metboxy" should be -- 6-methoxy --
Line 62  "(2,4-dichlbro-" should be -- (2,4-dichloro- --

Column 31
Line 6   "4-benzylpiperazsn-1-yl" should be -- 4-benzylpiperazin-1-yl --
Line 24  "5methoxyphenyl" should be -- 5-methoxyphenyl --
Line 27  "a mino" should be -- amino --

Column 33
Line 28  ")ammo]" should be -- )amino] --

Column 34
Line 2   ") -3-furyl" should be -- )-3-furyl --
Line 7   "-}5-" should be -- -{5- --
Line 9   "-3-carbonitrtle" should be -- -3-carbonitrile --
Line 16  "{[4-{2-" should be -- {[4-(2- --

Signed and Sealed this

Thirty-first Day of March, 2009

JOHN DOLL
*Acting Director of the United States Patent and Trademark Office*